US012420111B2

(12) United States Patent
Flynn et al.

(10) Patent No.: US 12,420,111 B2
(45) Date of Patent: Sep. 23, 2025

(54) ROTATING SHIELD BRACHYTHERAPY APPARATUS AND METHOD

(71) Applicant: UNIVERSITY OF IOWA RESEARCH FOUNDATION, Iowa City, IA (US)

(72) Inventors: Ryan T. Flynn, Iowa City, IA (US); Quentin E. Adams, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 752 days.

(21) Appl. No.: 17/440,375

(22) PCT Filed: Mar. 18, 2020

(86) PCT No.: PCT/US2020/023276
§ 371 (c)(1),
(2) Date: Sep. 17, 2021

(87) PCT Pub. No.: WO2020/191007
PCT Pub. Date: Sep. 24, 2020

(65) Prior Publication Data
US 2022/0184416 A1 Jun. 16, 2022

Related U.S. Application Data

(60) Provisional application No. 62/820,575, filed on Mar. 19, 2019.

(51) Int. Cl.
*A61N 5/10* (2006.01)
(52) U.S. Cl.
CPC ......... *A61N 5/1007* (2013.01); *A61N 5/1002* (2013.01); *A61N 2005/1009* (2013.01);
(Continued)

(58) Field of Classification Search
CPC .. A61N 5/1007; A61N 5/1002; A61N 5/1001; A61N 5/10; A61N 5/01;
(Continued)

(56) References Cited

U.S. PATENT DOCUMENTS 6,416,492 B1* 7/2002 Nielson ............... A61N 5/1002
600/467
9,795,804 B2* 10/2017 Van Appeldoorn ....... G01T 1/02
(Continued)

OTHER PUBLICATIONS

International Search Report and Written Opinion were mailed on Jun. 12, 2020 by the International Searching Authority for International Application No. PCT/US2020/23276 filed on Mar. 18, 2020 and published as WO2020191007 (Applicant—University of Iowa Research Foundation) (7 pages).
(Continued)

*Primary Examiner* — Samuel G Gilbert
(74) *Attorney, Agent, or Firm* — Ballard Spahr LLP

(57) ABSTRACT

A rotating shield brachytherapy (RSBT) apparatus includes a radiation source, at least one applicator, a catheter, a catheter drive assembly, a robotic positioning system, and a connection system. The applicator(s) is configured to be inserted or implanted into a patient. A distal end portion of the catheter has at least one radiation shield and is configured to receive a wire-mounted radiation source. The catheter drive assembly causes helical motion of the catheter and engages the proximal end portion of the catheter to selectively rotate the catheter about a longitudinal axis. The robotic positioning system aligns the catheter drive assembly, in both position and angular orientation at a modifiable rate, with the applicator(s), or to any programmed point in space. The connection system couples the catheter drive assembly to the applicator(s), and further decouple the catheter drive from the applicator(s).

20 Claims, 13 Drawing Sheets a. Catheter Drive Assembly, cover off

(52) U.S. Cl.
CPC .............. *A61N 2005/1018* (2013.01); *A61N 2005/1025* (2013.01); *A61N 2005/1094* (2013.01)

(58) Field of Classification Search
CPC ................ A61N 5/00; A61N 5/1014; A61N 2005/1018; A61N 2005/1008
See application file for complete search history.

(56) References Cited

U.S. PATENT DOCUMENTS

| | | |
|---|---|---|
| 2004/0010301 A1* | 1/2004 | Kindlein .............. A61N 5/1007 607/101 |
| 2007/0106108 A1 | 5/2007 | Hermann et al. |
| 2008/0167750 A1 | 7/2008 | Stahler et al. |
| 2014/0296611 A1 | 10/2014 | Schwartz |
| 2015/0367144 A1 | 12/2015 | Flynn et al. |
| 2017/0173362 A1 | 6/2017 | Lamoureux et al. |
| 2019/0126064 A1* | 5/2019 | Flynn ................. A61N 5/1027 |

OTHER PUBLICATIONS

International Preliminary Report on Patentability was mailed on Sep. 16, 2021 by the International Searching Authority for International Application No. PCT/US2020/23276 filed on Mar. 18, 2020 and published as WO2020191007 (Applicant—University of Iowa Research Foundation) (5 pages).

* cited by examiner b. Catheter Drive Assembly, cover on

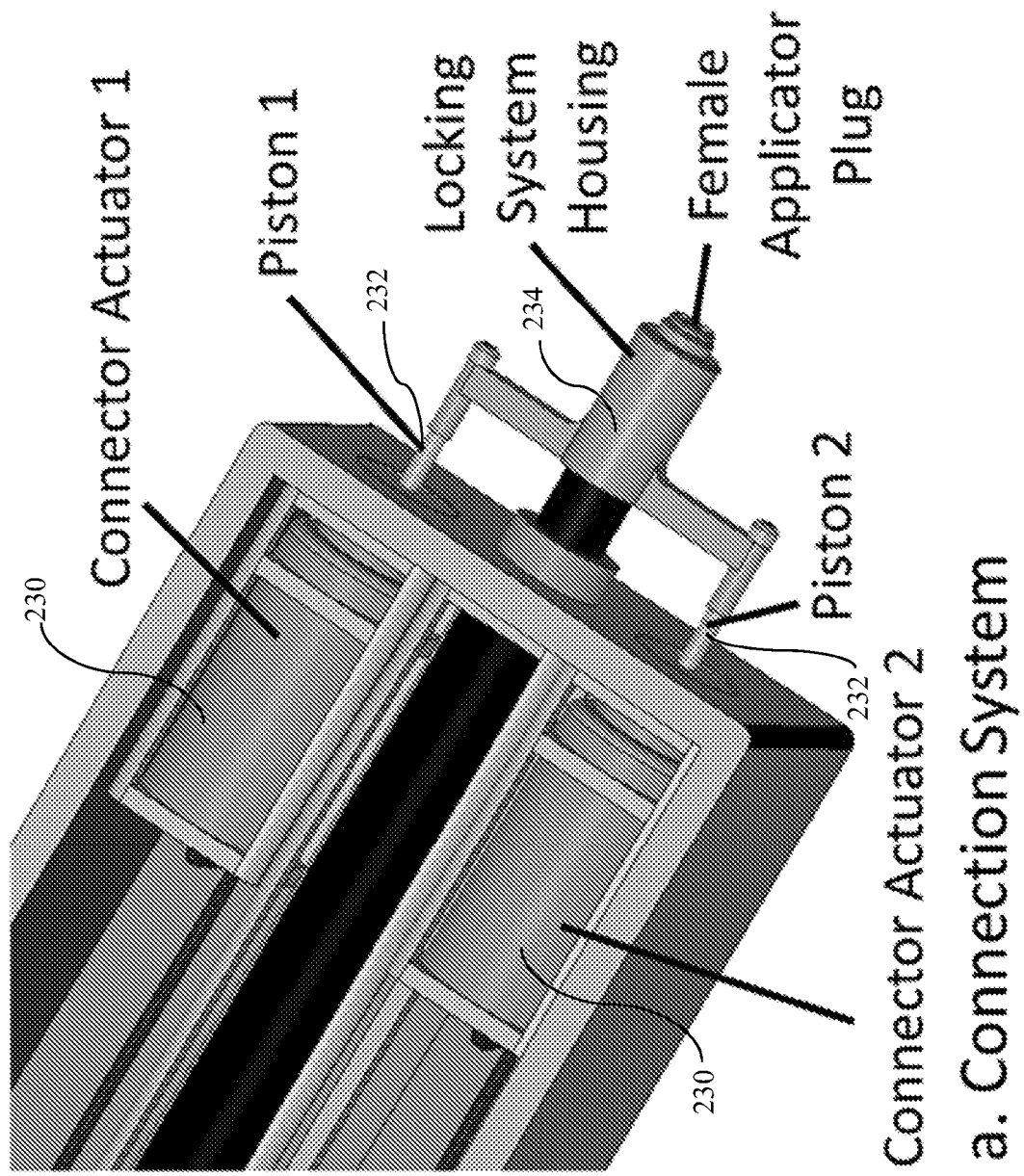

b. Connection System with Applicator

ROTATING SHIELD BRACHYTHERAPY APPARATUS AND METHOD

CROSS-REFERENCE TO RELATED APPLICATION

This is a U.S. National Phase Application of International Application No. PCT/US2020/023276, filed Mar. 18, 2020, which claims priority to and the benefit of the filing date of U.S. Provisional Patent Application No. 62/820,574, filed Mar. 19, 2019. The entirety of each of these applications is hereby incorporated by reference herein.

STATEMENT OF GOVERNMENT SUPPORT

This invention was made with government support under R01 EB020665 and R41 CA210737 awarded by the National Institutes of Health. The government has certain rights in the invention.

FIELD

This application relates to apparatuses and methods for brachytherapy treatment.

BACKGROUND

Standard prostate cancer treatments have excellent long-term tumor control but have significant toxicity and are inconvenient for patients. Prostate cancer is the most common non-skin cancer in men, with nearly 175,500 expected new diagnoses in 2019 in the U.S. alone. Approximately 11% of men are expected to be diagnosed with prostate cancer in their lifetime. Most prostate cancer patients have localized prostate cancer and, depending on their risk classification, can be offered a variety of definitive treatment options including surgery, external beam radiotherapy (EBRT), low-dose-rate brachytherapy (LDR-BT), and high-dose-rate brachytherapy (HDR-BT). Androgen deprivation therapy and active surveillance can also be offered in very low risk category patients. Although long-term (10+ year) biochemical disease-free survival is high and tends to increase with radiation dose delivered, nearly 32,000 men in the U.S. are expected to die of prostate cancer in 2019. While achieving tumor control is paramount, prostate cancer patients may live with the side effects of their treatment for decades, and anticipated side effects play a strong role in treatment decisions. There is a critical need in the urology and radiation oncology fields for new and innovative prostate cancer treatment techniques with equal or greater tumor control probability than current techniques, and reduced toxicity.

Robotic surgery, intensity modulated radiation therapy (IMRT), and brachytherapy have excellent and similar long-term tumor control rates, but have widely-varying side effects, cost, and convenience levels for each patient. The preferred treatment for the prostate cancer therapy market is the one that best optimizes the side effects, cost, and patient convenience without compromising long-term tumor control rates. Robotic surgery requires on average about 4 hours in the operating room, a median 3-day hospital stay, has the highest erectile dysfunction rate, and has the highest urinary incontinence rate, which is the most dominant side effect affecting patients' preferences for a given treatment. IMRT is the most expensive, requires up to 45 outpatient clinic visits to complete, has the worst hematochezia complication rate, and salvage therapy in the event of local recurrence, including the option of surgery, is challenging as it results in nearly ubiquitous incontinence and erectile dysfunction. Multi-fraction high-dose-rate brachytherapy is resource-intensive and inconvenient for patients, and adoption of the HDR-BT technique for treating prostate cancer will likely continue to be slow unless a single-shot technique can be established.

Single-shot HDR-BT is a low-toxicity, high-convenience treatment for patients who are eligible for HDR-BT monotherapy, but long-term biochemical control is inferior to that of conventional fractionation regimens. Conventional HDR-BT can be delivered conveniently, in one outpatient treatment, with a risk of side effects as low as or lower than any other method. Toxicity results for single-shot HDR-BT monotherapy have been low, with 0-9% rates of grade 3 or higher toxicity. Biochemical control for low- and intermediate-risk prostate cancer patients treated with single-shot HDR-BT, however, has been lower than that typically observed for conventionally-fractionated treatments. For conventional treatments of multi-fraction HDR-BT, LDR-BT, and EBRT+brachytherapy, reported biochemical control percentages are above 97% for 5 years post-treatment and beyond. Long-term biochemical relapse-free survival rates for single-shot HDR-BT were recently reported by one group to be 82% at 6 years for low-risk (n=22) and intermediate-risk (n=34) patients for a prescription dose of 20.5 Gy. Another group reported a biochemical control rate of 73.4% at 5 years for low-risk (n=40) and intermediate-risk (n=28) patients with a prescription dose of 19 Gy. Both groups claimed results could be improved through dose escalation. It is well-known that increasing prostate dose increases biochemical relapse-free survival, but increasing dose increases risk of treatment complications. Prostate RSBT has the potential to dramatically increase radiation dose to the prostate, which would be expected to improve biochemical control rates, without increasing dose to the bladder or rectum beyond their threshold doses, and while holding urethra dose to the same levels as with HDR-BT monotherapy. The rationale for considering dose escalation with prostate RSBT is thus to maximize biochemical relapse-free survival without increasing complication rates.

For patients who are ineligible for HDR-BT monotherapy, single-shot HDR-BT as a boost therapy for external beam radiotherapy provides excellent long-term biochemical control, but urethra toxicity rates are relatively high. For patients with advanced prostate cancer staging level or risk group, indicating greater disease spread, and thus making them ineligible for RSBT monotherapy, an HDR-BT boost is intended to increase the total dose delivered to the prostate beyond that possible with EBRT alone. A limitation of combined EBRT and HDR-BT is that the genitourinary toxicity increases beyond that of EBRT alone, and a correlation has been reported between urethra $D_{10}$ (minimum dose to the hottest 10% of the urethra) and the rate of grade 2 or greater genitourinary toxicity, as well as decreased Expanded Prostate Cancer Index Composite urinary domain score. The rationale for RSBT in the context of urethra-sparing is to decrease urethra $D_{10}$ while minimally compromising dose coverage of the remaining prostate, thus theoretically decreasing the toxicity of the combined EBRT and brachytherapy approach without decreasing biochemical control rates.

Accordingly, improved methods for treating diseases such as prostate cancer are desired.

SUMMARY

Disclosed herein, in one aspect, is a rotating shield brachytherapy (RSBT) apparatus. The RSBT apparatus can comprise a radiation source, at least one applicator that is configured to be inserted or implanted into a patient, and a catheter having an outer surface and opposed proximal and distal end portions and a longitudinal axis extending along the length of the catheter. The distal end portion of the catheter can comprise at least one radiation shield. The radiation shield can be configured to receive a wire-mounted radiation source from an afterloader device. A catheter drive assembly can be configured to cause helical motion of the catheter. The catheter drive assembly can be configured to engage the proximal end portion of the catheter to selectively rotate the catheter about the longitudinal axis. A robotic positioning system can be configured to align the catheter drive assembly, in both position and angular orientation at a modifiable rate, with the at least one applicator, or to any programmed point in space. A connection system can be configured to couple the catheter drive assembly to the at least one applicator, and further configured to decouple the catheter drive from the at least one applicator. When the at least one applicator is coupled to the catheter drive assembly, the catheter can be configured to be advanced into, and out of, the at least one applicator at a variable rate through operation of the catheter drive assembly.

A method of use thereof is further disclosed.

Additional advantages of the disclosed system and method will be set forth in part in the description which follows, and in part will be understood from the description, or may be learned by practice of the disclosed system and method. The advantages of the disclosed system and method will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed apparatus, system, and method and together with the description, serve to explain the principles of the disclosed apparatus, system, and method.

FIG. 5A is a perspective view of a connection system for the catheter drive assembly;

DETAILED DESCRIPTION

Figure 1:
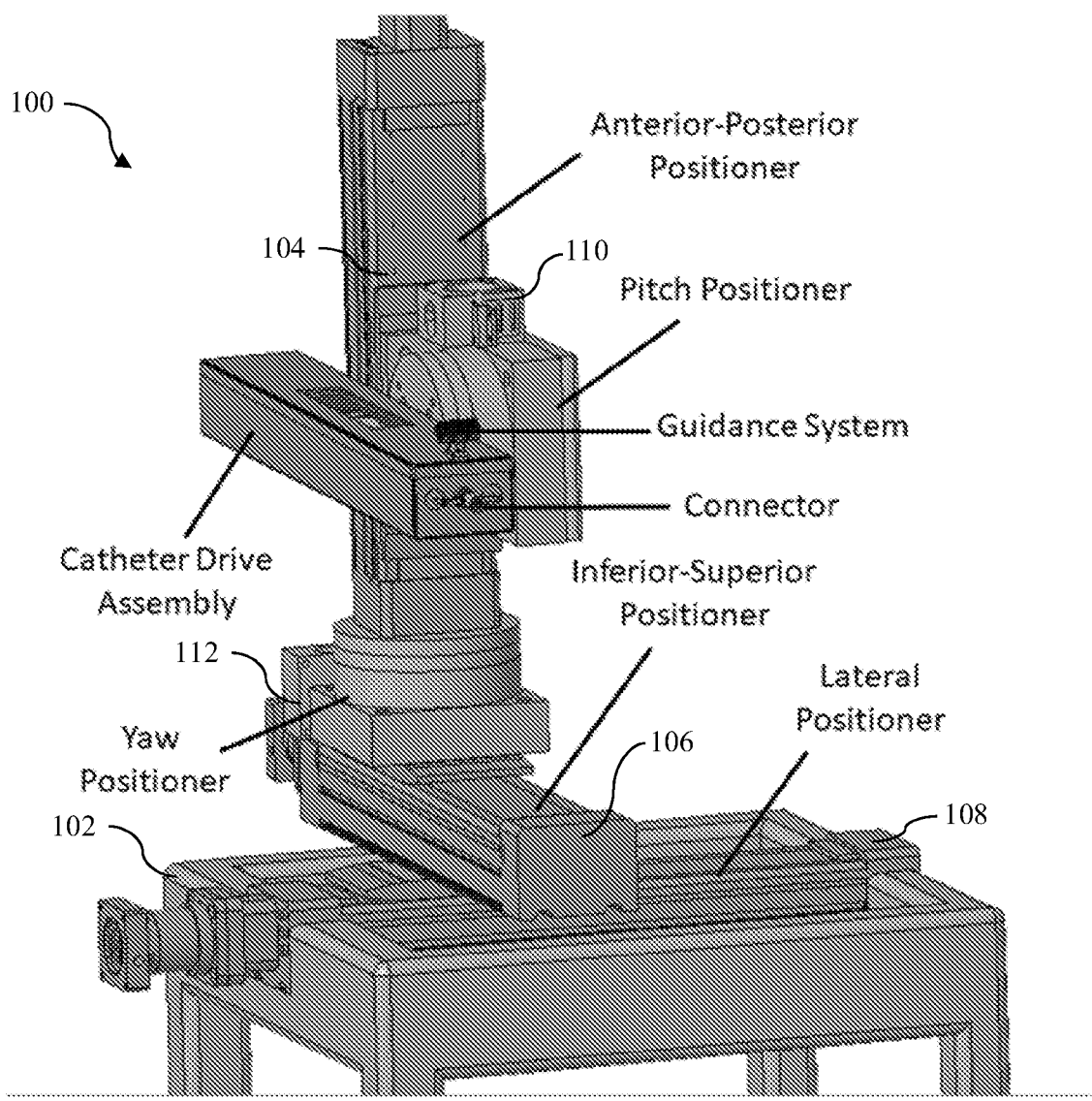
FIG. 1 illustrates perspective view of a robotic rotating shield brachytherapy therapy (RSBT) delivery system in accordance with embodiments discussed herein.

The disclosed system and method may be understood more readily by reference to the following detailed description of particular embodiments and the examples included therein and to the Figures and their previous and following description.

A. Definitions

It is to be understood that the terminology used herein is for the purpose of describing particular embodiments only, and is not intended to limit the scope of the present invention which will be limited only by the appended claims.

It must be noted that as used herein and in the appended claims, the singular forms "a", "an," and "the" include plural references unless the context clearly dictates otherwise. Thus, for example, reference to "an elbow" includes a plurality of such elbows, and reference to "the elbow" is a reference to one or more joints and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

When used herein as an approximation of a particular value or characteristic, the term "substantially" can refer to values or characteristics that are within 15%, within 10%, within 5%, or within 1% of the stated value or characteristic (above or below). For example, when two components are "substantially aligned," it is contemplated that components that are 15%, 10%, 5%, or 1% angled relative to a straight configuration can be included.

Unless defined otherwise, all technical and scientific terms used herein have the same meanings as commonly understood by one of skill in the art to which the disclosed apparatus, system, and method belong. Although any apparatus, systems, and methods and materials similar or equivalent to those described herein can be used in the practice or testing of the present apparatus, system, and method, the particularly useful methods, devices, systems, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications may be referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Rotating Shield Brachytherapy Apparatus and Method

Disclosed herein is a rotating shield brachytherapy apparatus and method. Referring to FIG. 1, an RSBT system 100 can facilitate the positioning of an afterloader-controlled, wire-mounted radiation source within the one or more shields to deliver the radiation dose in a clinically-reasonable timeframe. In the embodiment shown, the RSBT system 100 comprises a robotic positioning system 102 that positions a camera-guided catheter drive assembly 200. The camera-guided catheter drive assembly 200 can connect to one applicator 300 (FIGS. 6A and 6B) at a time and can drive a partially-shielded radiation source in a helical manner into the applicator, accounting for the applicator's position and orientation. Positioning of the catheter drive assembly 200 can be accomplished using one or more linear positioners, with three shown in FIG. 1 (an anterior-posterior linear positioner 104, an inferior-superior linear positioner 106, and a lateral linear positioner 108), and one or more angular positioners, with two shown in FIG. 1 (a yaw angular positioner 110 and a pitch angular positioner 112). One or more applicators can be implanted into the patient, and the system can be capable of radiation delivery through the applicators in series.

Figures 6A, 6B:
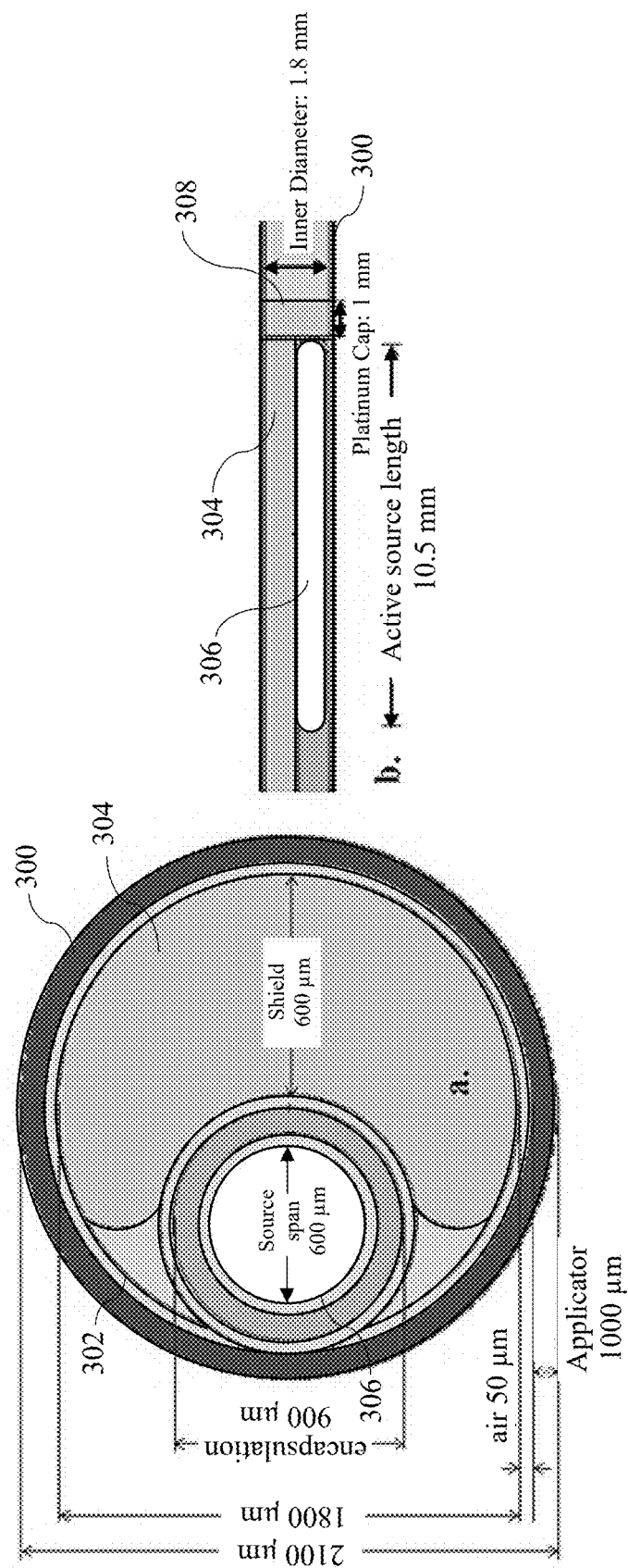
FIGS. 6A and 6B illustrate an axial view diagram and a sagittal view diagram, respectively, of the applicator, catheter, partial shield, and radiation source at the distal end of a catheter inserted into an applicator.

The applicators (e.g., needles) implanted in the patient can be constructed of a variety of materials, and different materials have different advantages and disadvantages. A diagram of the applicator 300, a catheter 302, a partial shield 304, and a radiation source 306 at the distal end 308 of the catheter inserted into the applicator is shown in FIGS. 6A and 6B. A nitinol (NiTi) applicator, for example, is more mechanically flexible than a stainless steel applicator and can optionally have a very thin wall of about 100 microns. Plastic applicators can have thicker walls, usually 200 microns or greater, which increases overall applicator diameter for the same shielded catheter relative to nitinol applicators, but can provide greater mechanical flexibility. In some embodiments, the robotic RSBT system can have nitinol applicators.

Figure 4:
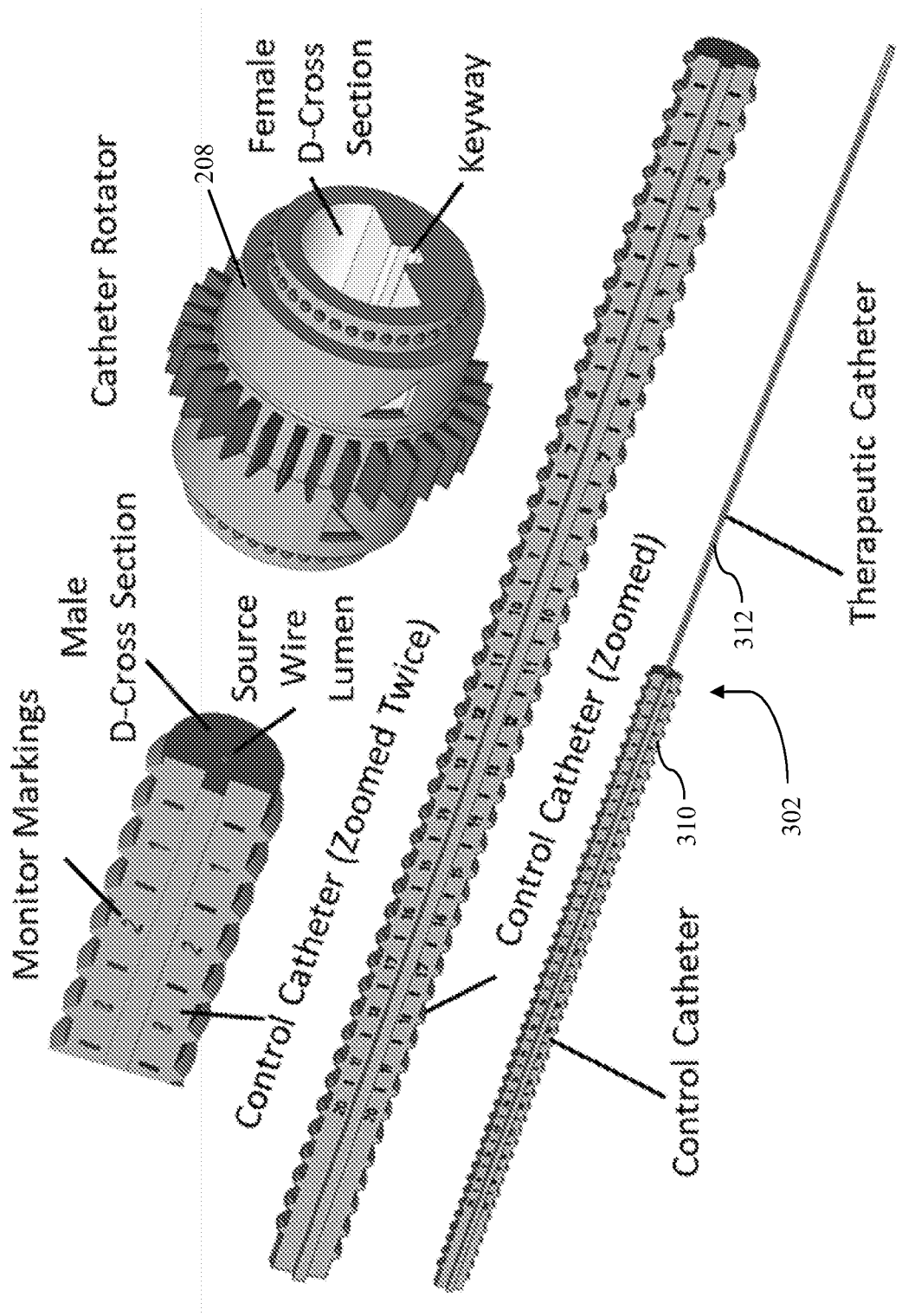
FIG. 4 is a perspective view of several components of the catheter drive assembly as in FIG. 2A.

Referring to FIG. 4, the catheter can comprise two major components that are rigidly connected to each other: a proximal end portion and a distal end portion. Optionally, the proximal end portion can be provided as a threaded control catheter component 310, and the distal end portion can be provided as a therapeutic catheter component 312. The exemplary embodiment of a threaded control catheter component 310 and a therapeutic catheter component 312 is described below and depicted in the drawings. However, it is contemplated that other configurations of proximal and distal end portions can be provided.

The therapeutic catheter component 312 can be advanced into the applicator(s) 300, and the control catheter component 310 can be proximal to the applicator(s) 300 and can have a greater diameter than the therapeutic catheter component 312. The therapeutic catheter component comprises, contains, or has connected to it, one or more partial shields 304 (FIGS. 6A and 6B). The therapeutic catheter component can travel the length of each applicator and receive a wire-mounted radiation source 306 from an afterloader. In one embodiment, the catheter comprises a nitinol tube with shields comprising platinum, although other catheter materials are possible, such as stainless steel or plastic, and other shield materials are possible, such as tungsten, tungsten carbide, uranium, osmium, iridium, gold, lead, bismuth, iron, molybdenum, and the like.

Figure 2A:
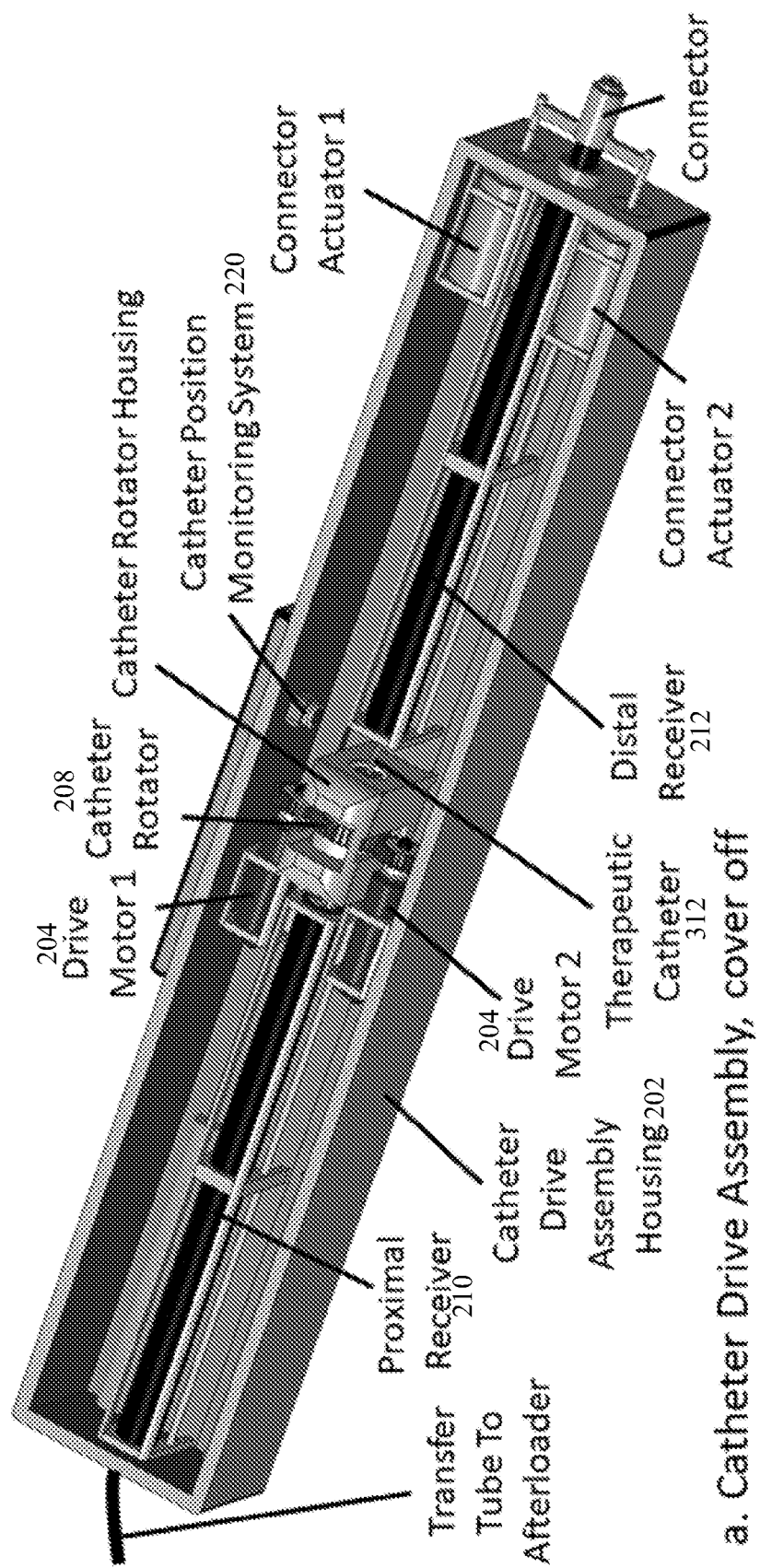
FIG. 2A is a perspective view of a catheter drive assembly for the RSBT delivery system as in claim 1.
Figure 2B:
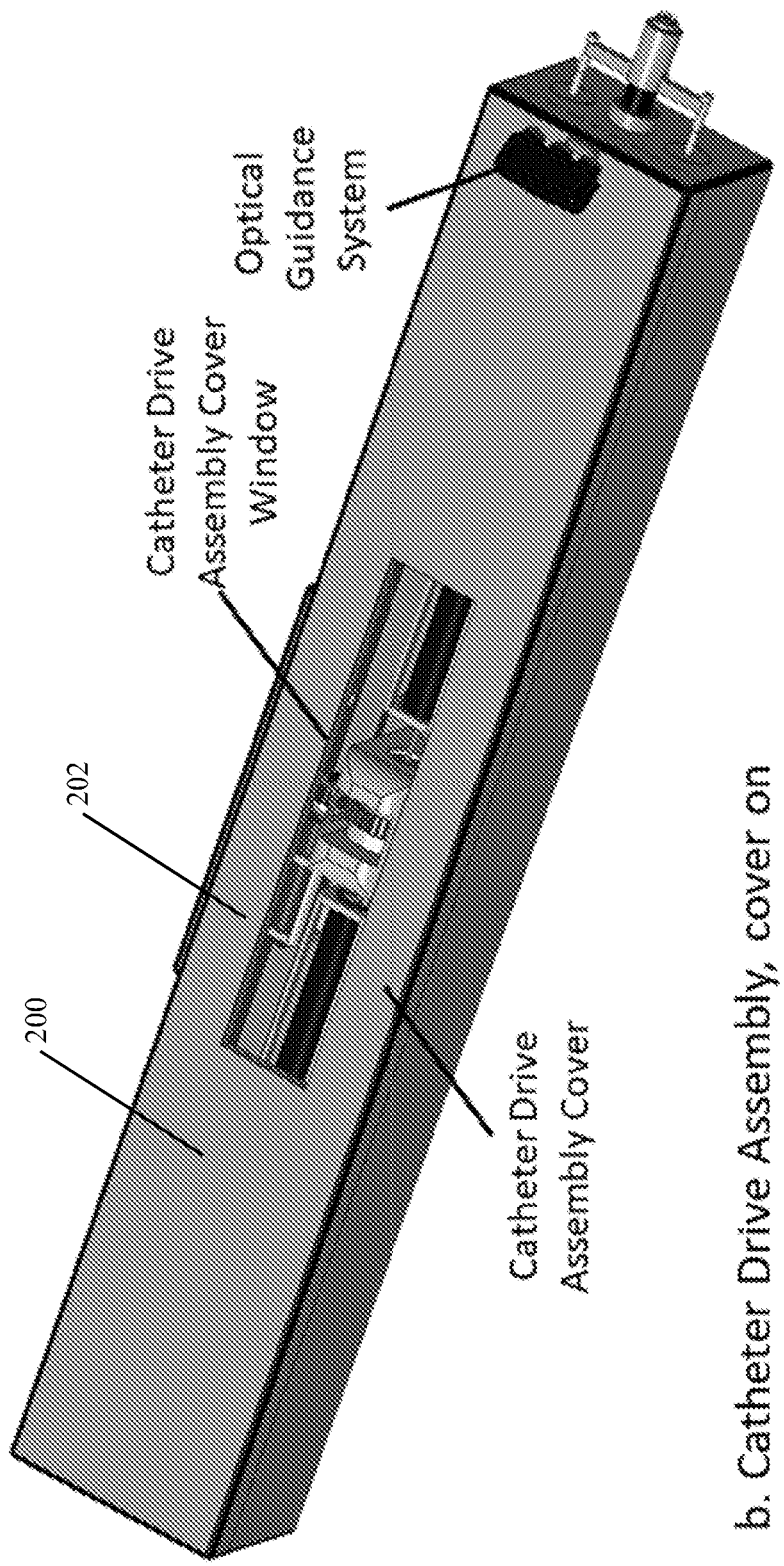
FIG. 2B is a perspective view of the catheter drive assembly as in FIG. 2A with a cover thereon.
Figure 3:
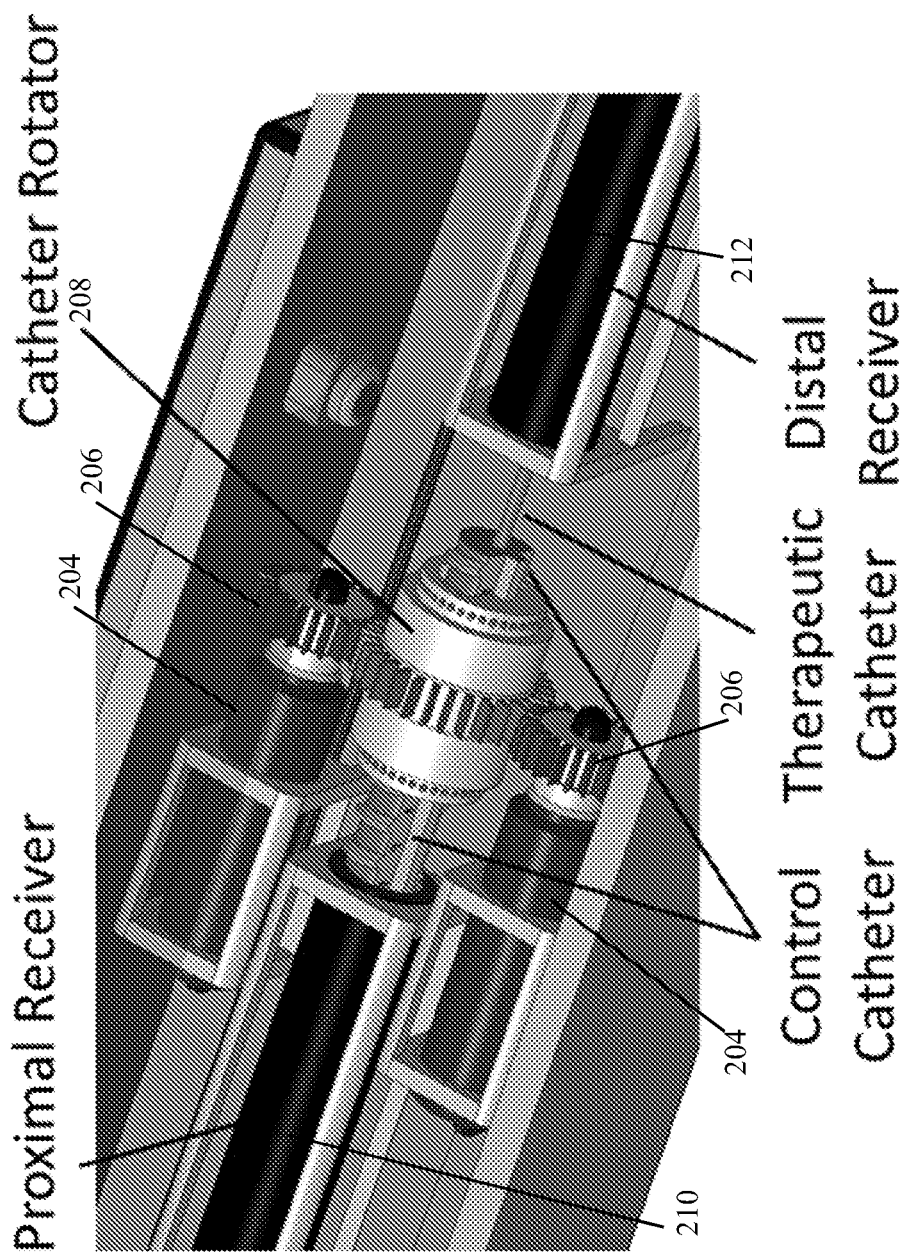
FIG. 3 is a close-up partial perspective view the catheter drive assembly as in FIG. 2A.

The catheter drive assembly 200, shown in FIG. 2A with a cover off and in FIG. 2B with the cover in place, is a means of advancing and retracting the therapeutic catheter into the one or more applicators in series. According to some aspects, the catheter drive assembly 200 can be an independent functional component that can be dissociated en bloc from the robotic positioning system without affecting functionality of either component. Accordingly, the catheter drive assembly 200 can be substituted for a replacement, or similarly configured, catheter drive assembly. The catheter drive assembly 200 can be contained within a housing 202 that supports one or more drive motors 204, with two or more drive motors providing redundancy. The drive motors 204 can rotate respective gears 206 that engage corresponding teeth of a catheter rotator 208. The catheter rotator 208 can define a non-circular hole therethrough that matches (or mates with) the cross-sectional shape of the control catheter 310, which, in one embodiment, is a D-shape (as shown in FIG. 4). The non-circular cross-sectional shape enables concurrent catheter rotation along with the catheter rotator when the drive motors are activated. The revolution of the catheter rotator, due to the threading on the control catheter, can cause simultaneous rotational and longitudinal motion of the catheter. That is, the catheter drive assembly can define female threads that engage the male threads of the control catheter so that rotation between the female threads of the catheter drive assembly and the control catheter causes longitudinal movement of the catheter within the applicator, and the control catheter can slide longitudinally within the catheter rotator 208. In one embodiment, the flat lateral face of the control catheter is marked in a manner such that a catheter position monitoring system 220 can use an optical means to determine the longitudinal and rotational position of the catheter in real-time throughout the radiation delivery process. The monitoring system can be interfaced with a computer (e.g., computing device 1001 of FIG. 10)

and can be configured with a feedback loop in which the catheter position is corrected to decrease the difference between the expected and actual catheter positions.

In one embodiment, the catheter drive assembly 200 comprises a proximal receiver tube 210 and a distal receiver tube 212 that provide mechanical guidance for the control catheter 302 upon rotational advancement or retraction. The proximal receiver tube has an inner surface that is at least partially helically threaded, causing the control catheter to advance in a helical pattern when the catheter rotator rotates. When the therapeutic catheter is fully retracted proximally, i.e., fully contained within the catheter drive assembly, the control catheter can reside within the proximal receiver tube, and the therapeutic catheter can reside within the distal receiver tube. The distal receiver tube can contain a distal lumen, mechanically positioned such that the fully retracted therapeutic catheter remains aligned (or substantially aligned) with the inner lumen of the connector that connects the catheter drive assembly with the applicators. When the therapeutic catheter is fully inserted into an applicator by actuation of the drive motors, the control catheter 300 can be advanced down the proximal receiver tube 210 and mostly contained within the distal receiver tube 212. The proximal end of the distal receiver tube 212 can contain a view port 216 of sufficient area for the catheter position monitoring system to observe the catheter's rotational and longitudinal position.

Figure 5B:
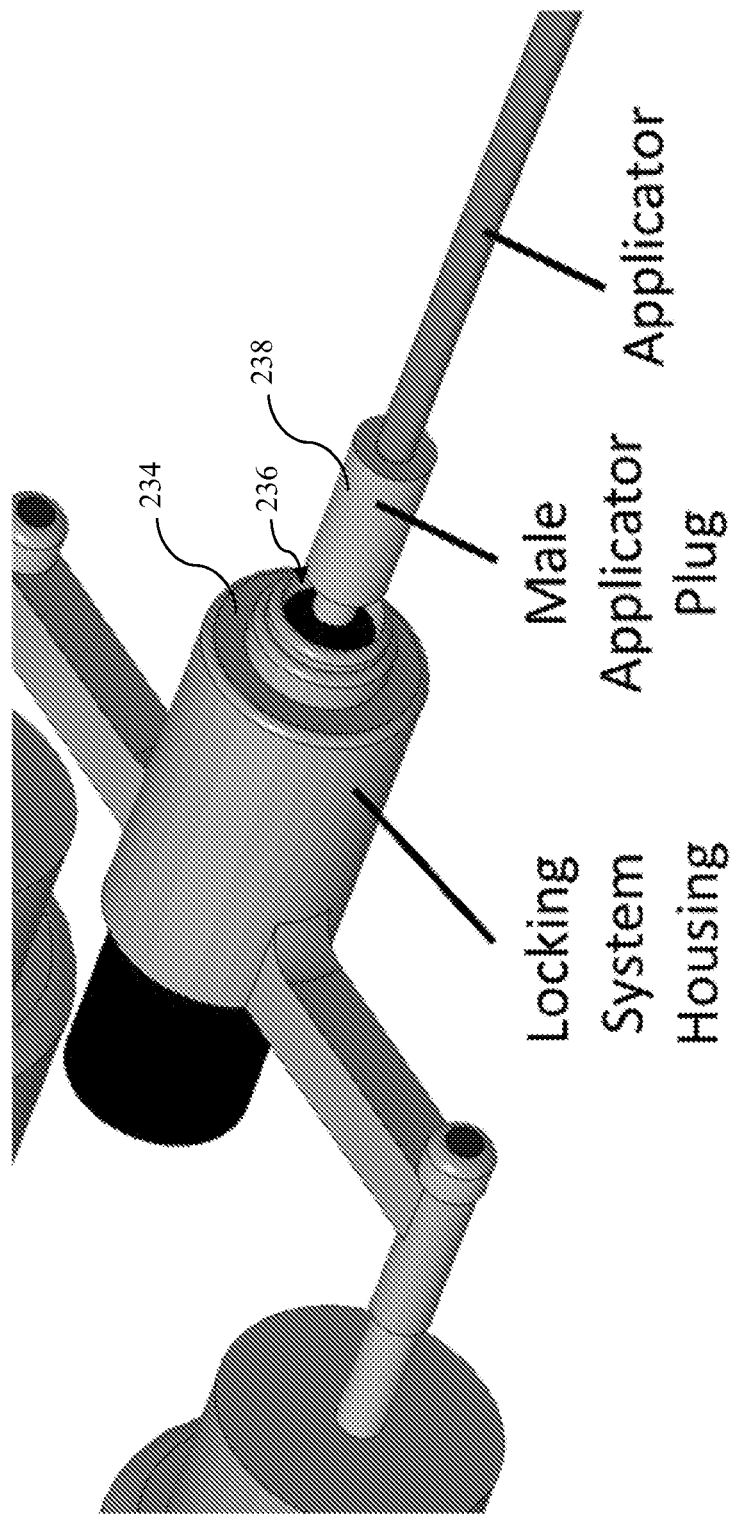
FIG. 5B is a perspective view of the connection system as in FIG. 5A with a connected applicator.

A connection system, shown in FIG. 5, can facilitate the adjoining and locking of the catheter drive assembly to an applicator. The connection system can comprise one (or more for redundancy) actuator(s) 230 that, via actuator-specific pistons 232, retract a locking system housing 234. When the locking system housing is retracted, a female plug 236 is exposed that, after physical alignment, connects to a male plug 238 at the proximal end of the applicator 300 (FIGS. 6A and 6B). When the actuator(s) 230 returns the locking system housing, the applicator and catheter drive assembly are locked together, enabling the therapeutic catheter to advance into the applicator. Thus, in some optional aspects, the connection system can be configured as, or like, commercially available quick connect hydraulic fittings. For example, in one optional aspect, the female plug 236 can comprise a ball detent, wherein retraction of the locking system housing 234 releases the ball detent to enable receipt of the male plug 238 of the applicator 300. The male plug 238 can comprise at least one radially extending projection (e.g., a circumferential lip) that engages the ball detent so that when the locking system housing 234 returns, the ball detent can engage the radially extending projection to couple the applicator to the locking system housing. Thus, when coupled, the catheter drive assembly 200 can align with the applicator 300 so that the catheter 302 in the catheter drive assembly 200 is axially aligned with the interior of the applicator. However, it is contemplated that other conventional couplings, adapters, and/or fittings can be used, provided they permit the relative motion of the components disclosed herein. When radiation delivery through the applicator is complete, the locking system housing can be retracted again, disconnecting the male and female plugs. The catheter drive assembly can be retracted from the applicator, then aligned (or substantially aligned) with the next applicator, locked into place, and the delivery process can continue until no untreated applicator positions remain.

The connection of the catheter drive assembly to one or more applicators in series can be facilitated by a guidance system. The guidance system can determine the relative locations of all implanted applicators, enabling the system to physically identify the appropriate applicator and align the connector at the distal end of the catheter drive assembly with that applicator. The guidance system, in a feedback loop, can iteratively determine the position and orientation of the catheter drive assembly and therefore the connector, and a given applicator, with the accuracy of each determination increasing as the robot moves the connector closer to the applicator. The guidance system can be based on optical, electrical, and magnetic means for identifying one or more applicators and determining the positions and orientations of those one or more applicators. For example, a camera can detect markings on the applicators. In further aspects, the applicators can comprise magnets or electric field signatures (e.g., RFID tags) that are detectable via magnetic field sensors or electric field sensors, respectively. In further aspects, the guidance system could be based around another means of such determination. A combination of different means for determination of applicator identification, position, and orientation is possible. Combinations allow for enabling redundancy or optimization, such as using an optical means for applicator determination and an electrical means for applicator position and orientation determination. An example embodiment for an optically-based guidance system is shown in FIG. 2B.

In some aspects, it is contemplated that the catheter drive assembly can comprise a locking mechanism that can enable rotational movement of the catheter while inhibiting or preventing longitudinal movement of the catheter. For example, in some optional aspects, the catheter drive assembly can rotationally decouple the proximal receiver from the housing 202 so that the proximal receiver can rotate freely within the housing 202 (so that the proximal receiver and the control catheter can rotate together). Thus, the catheter rotator can drive the control catheter rotationally without causing longitudinal movement of the catheter.

Using a treatment planning system and the RSBT apparatus disclosed herein, it is contemplated that delivery of robotic RSBT for a prostate cancer patient can proceed as follows:

(1) Applicators (needles) can be placed in the patient through a locking template by a physician utilizing an image guidance system, such as ultrasound;

(2) Images of the patient anatomy and implanted applicators may be obtained using computed tomography or magnetic resonance imaging modalities, but ultrasound images may be sufficient for treatment planning;

(3) Images from step (1), step (2), or both step (1) and (2) can be imported into the primary treatment planning system (e.g., VARIAN BRACHYVISION, ELEKTA ONCENTRA, or ECKERT & ZIEGLER SAGIPLAN) associated with the afterloader or contour-generating software, and a physician or medical physicist then contours target volumes and organs-at-risk.

(4) Contours can be imported into the primary treatment planning system, and applicator positions are reconstructed;

(5) Contours and applicator positions can be exported from the primary treatment planning system and imported into the RSBT treatment planning system;

(6) RSBT treatment plan is generated using the RSBT treatment planning system;

(7) Physician approval for the RSBT treatment plan is received;

(8) Patient-specific quality assurance is performed as required according to local policies and regulations;

(9) Dwell position and dwell time instructions for all applicators can be exported to the afterloader, and RSBT rotating catheter instructions for each applicator are exported for the RSBT catheter drive assembly;

(10) The template through which the applicators were inserted can be locked by the template-specific means, holding the applicators physically in place such that their positions are not disturbed by connection of the catheter drive assembly to the applicators;

(11) The afterloader can be connected to the proximal end of the control catheter via a transfer tube, allowing the radiation source to enter the therapeutic catheter and deliver the treatment;

(12) Pre-delivery quality assurance checks can be performed by the clinical staff;

(13) If any applicators remain through which radiation needs to be delivered, the method can go to step (14). Otherwise, the method can go to step (17).

(14) For the next applicator through which to deliver radiation, the RSBT robot, using the guidance system, can align and orient the catheter drive assembly with the applicator, and locks the catheter drive assembly to the applicator using the connection system.

(15) The catheter drive motor(s) can be engaged, causing the catheter to rotate and advancing the therapeutic catheter to the distal end of the current applicator;

(16) RSBT can be delivered through the current applicator as follows:

(16.A) Radiation source can be moved to next shield (or shield-free) position in the therapeutic catheter;

(16.B) Drive motor(s) can activate, moving the therapeutic catheter helically through applicator, with time spent at each position along the helix dictating the amount of radiation dose emitted at the corresponding position and direction;

(16.C) Radiation source can be retracted out of the rotating catheter;

(16.D) If treatment for the current applicator is complete, the method can proceed to step (13); otherwise, the method can proceed step (16.E)

(16.E) The drive mechanism can advance the rotating catheter to the distal end of the applicator;

(16.F) Steps 16.A-16.E can be repeated as necessary;

(17) Post-treatment brachytherapy processes can be completed.

Providing safe and accurate RSBT delivery can require a quality assurance (QA) technique for ensuring the therapeutic catheter is located at the appropriate angular and depth location inside the catheter as a function of time. Special applicators could be used for this purpose, called QA applicators, which comprise optically transparent or translucent portions for visualization and measurement of the depth and angular orientation of the rotating catheter inside the applicators. The inner lumens of the QA applicators can be exact mechanical copies of the corresponding clinical applicators. As a quality assurance step, the RSBT drive system can be used to advance the rotating catheter to one or more positions inside the QA applicator and compare the expected versus measured rotating catheter positions. If the expected and measured rotating catheter positions are within some tolerance limit of each other, such as 1 mm and 7°, the QA test can be deemed passed, and the corresponding clinical applicator and rotating catheter are deemed safe for clinical usage.

A QA control catheter can also verify the position of the radiation source wire, or dummy (non-radioactive) wire inside the catheter. The QA catheter can have the same construction as the clinical catheter used for radiation delivery, except with a transparent or translucent portion with markings that enable the location of the radiation source wire or dummy wire inside the rotating catheter to be precisely determined.

Figure 7A:
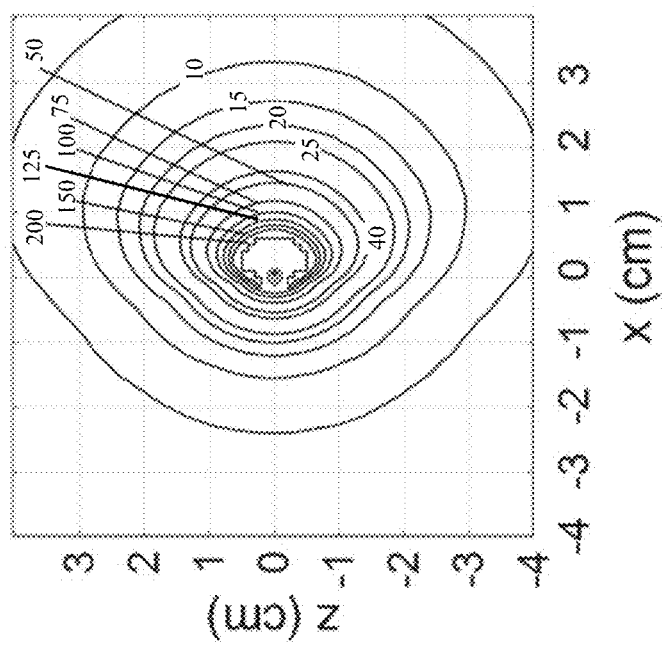
FIGS. 7A and 7B illustrates dose rate distributions for a partially-shielded $^{169}$Yb radiation source in a prostate cancer RSBT needle, normalized to 100% at 1 cm from the source center in water on the unshielded side, where 7A is an axial view and 7B is a sagittal view.
Figure 7B:
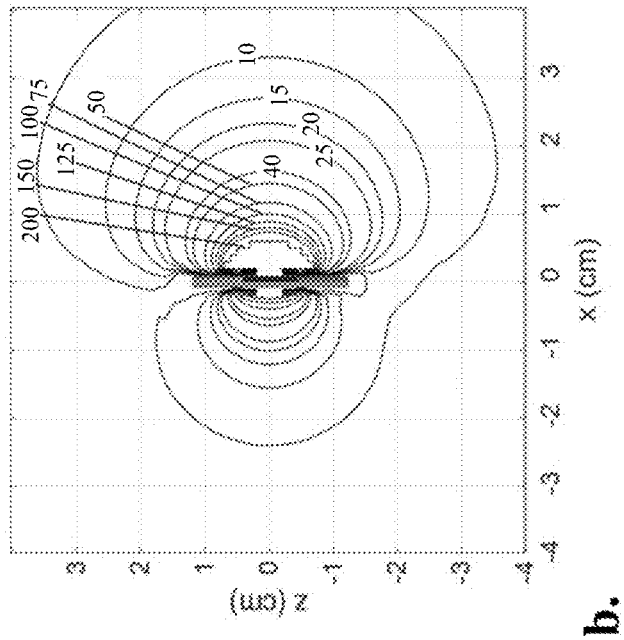

The capability of the herein-disclosed $^{169}$Yb-based robotic RSBT system to deliver escalated prostate doses relative to those possible with HDR-BT without violating bladder, rectum, and urethra doses has been demonstrated in a modeling study, along with the capability to minimize urethral dose without compromising prostate dose coverage. A data set of 26 patients was considered, which was used in a previously-published study on the dosimetric effectiveness of RSBT for prostate cancer. All of the patients were clinically treated with HDR-BT, and radiation oncologists generated contours for the planning target volume (PTV), urethra, bladder, and rectum, which had mean (±one standard deviation) volumes of 61.7±14.3 cm$^3$, 2.2±0.7 cm$^3$, 60.6±28.7 cm$^3$, and 42.1±14.9 cm$^3$, respectively. The PTV was defined as the entire volume of the prostate with no additional margin added. A margin of 3 mm was added to the urethra contour to provide space for a dose gradient about the urethra. The clinically-used needle positions were used for the HDR-BT plans, and a median of 23 needles was used. Prostate RSBT needle models generated with MCNP are shown in FIG. 6, and the resulting normalized dose rate distributions are shown in FIG. 7. For each patient, the needles were manually re-arranged for the RSBT plans, placing several needles within a few mm of the urethra. This enabled effective use of the sharp directional dose gradients produced by partial shielding of the $^{169}$Yb for the RSBT plans, avoiding an unfair comparison with HDR-BT. Similarly, it was found important not to use the RSBT needle positions for the HDR-BT plans to avoid unfairly increasing urethra dose for those plans. The $^{169}$Yb source activity used in the simulations was 27 Ci, and the helical pitch was 5 mm, corresponding to 5 mm of therapeutic catheter longitudinal translation per rotation of the control catheter.

Two types of treatment plans for prostate RSBT were generated: dose escalation plans and urethra-sparing plans. The dose escalation plans represented single-shot RSBT monotherapy, in which patients are delivered as high a dose as possible in a single treatment fraction, with no other radiation therapy. Clinicians would not be restricted to this approach, as prostate dose escalation in the boost context is also contemplated, as well as a combination of dose escalation and urethra-sparing relative to conventional HDR-BT.

In the treatment planning process, a hyaluronic acid spacer injection was simulated for all patients to model the displacement between the PTV and the rectum, such that the distance between the PTV and rectum was 2 cm. The same optimization parameters used by Adams et al (2018), incorporated by reference below, were employed in the planning process, which was based on the POGS approach. For the dose escalation plans, HDR-BT dose was prescribed such that 90% of the PTV received 110% of the prescribed physical dose of 20.5 Gy, and the final RSBT plan was created by scaling the dwell times to maximize the physical dose delivered without exceeding the urethra $D_{10}$ that was obtained from the HDR-BT plan for the same patient. For the urethra-sparing plans, HDR-BT dose was prescribed such that 90% of the PTV received 110% of the prescribed physical dose of 15 Gy, and the final RSBT plan was created by scaling the dwell times to minimize urethra $D_{10}$ while matching the PTV $D_{90}$ from the HDR-BT plan. For the dose escalation plans, the increase in PTV $D_{90}$ compared with HDR-BT was the metric for RSBT improvement because it reflects the magnitude of dose escalation to the PTV that is possible with RSBT. In the urethra-sparing plans, the decrease in urethra $D_{10}$ compared with HDR-BT was the metric for RSBT improvement because it reflects the reduction in dose to the urethra that is possible with RSBT. Urethra, bladder, and rectum dose tolerances were derived from previous clinical results for HDR-BT monotherapy, boost therapy, and cervical cancer brachytherapy. For dose escalation the urethra, bladder, and rectum tolerances were $D_{10}$<22.6 Gy, $D_{2cc}$<20.7 Gy, and $D_{2cc}$<18.5 Gy, respectively, and for urethra-sparing they were $D_{10}$<16.5 Gy, $D_{2cc}$<12.9 Gy, and $D_{2cc}$<17.1 Gy, respectively.

Figure 8:
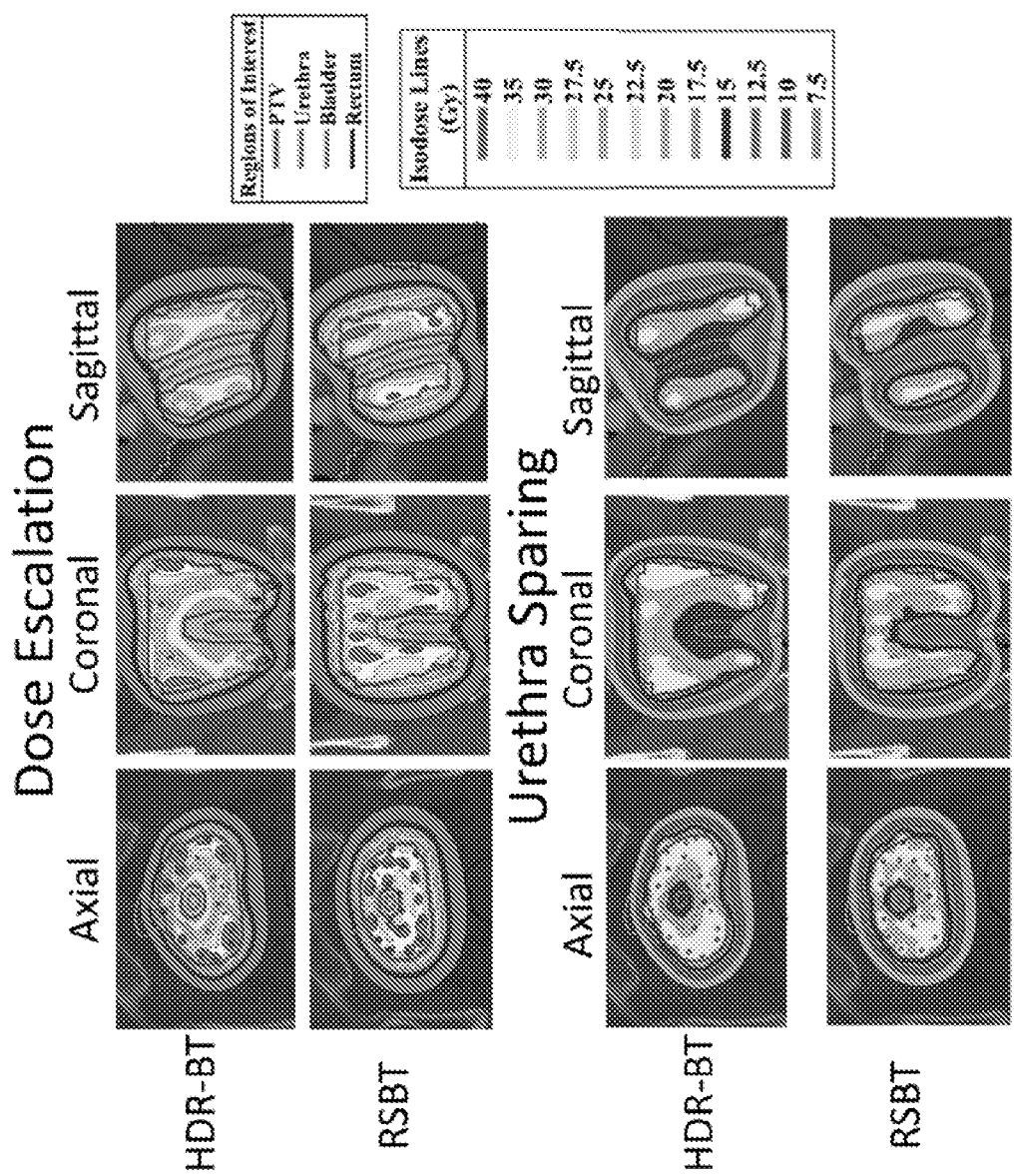
FIG. 8 illustrates dose distributions for a representative patient.
Figure 9A:
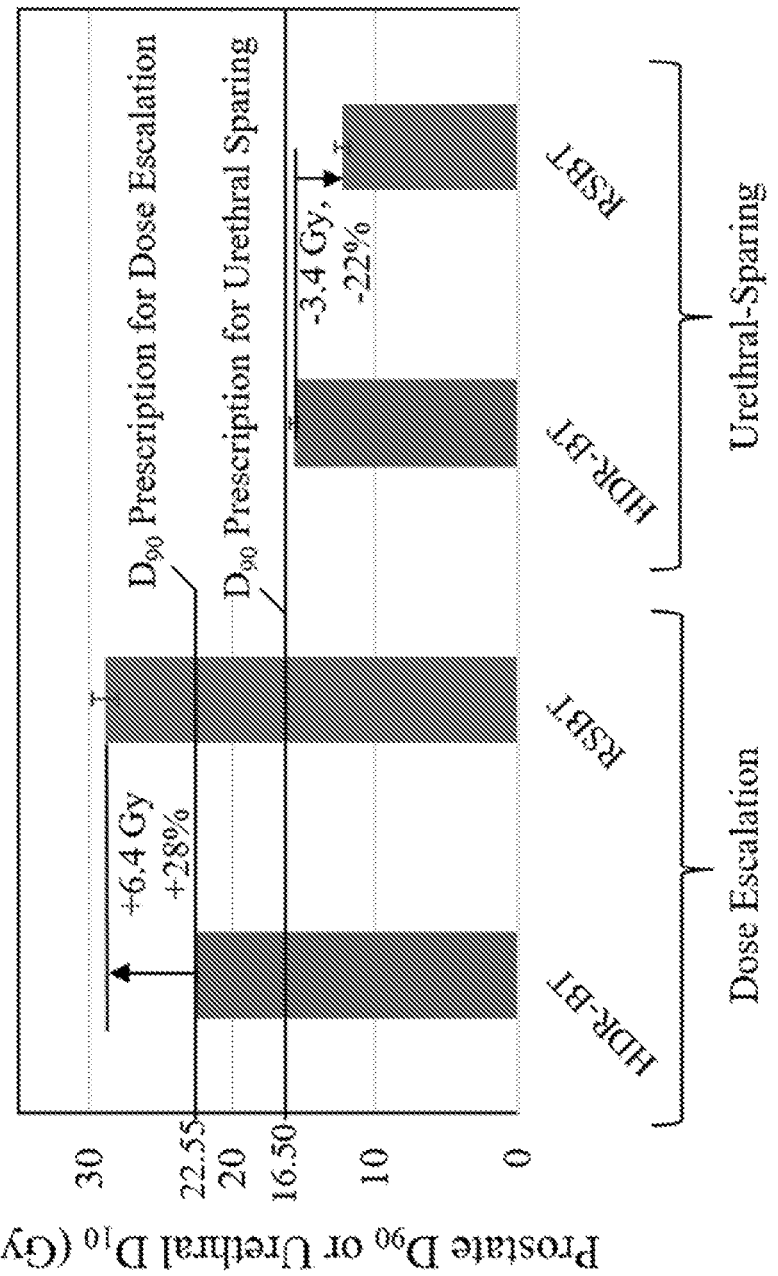
FIG. 9A illustrates prostate mean and standard deviation $D_{90}$ values for single-shot dose escalation and urethra $D_{10}$ values for single-shot urethra sparing (boost therapy) for 26 patients.
Figure 9B:
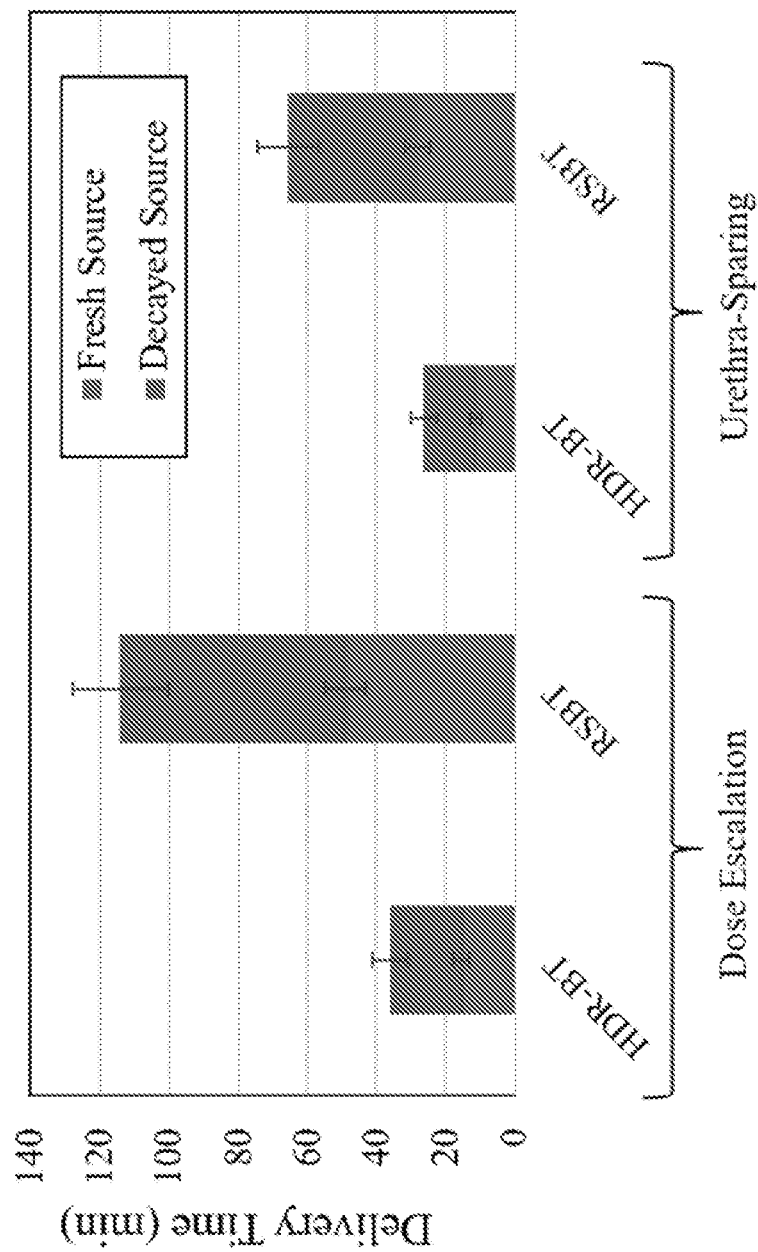
FIG. 9B illustrates delivery times for the delivery techniques of FIG. 9A.

Representative conventional HDR-BT and robotic RSBT dose distributions for one patient are shown in FIG. 8. Applicator (needle) locations are shown in the axial plane images. Dose from external beam radiotherapy is not included in the urethra sparing dose distributions. Comprehensive mean and standard deviation (over the 26 patients) prostate $D_{90}$ and urethra $D_{10}$ values are shown in FIG. 9A, and delivery times are shown in FIG. 9B. FIG. 9A illustrates prostate mean (bars) and standard deviation (whiskers) $D_{90}$-values for single-shot dose escalation (monotherapy) and urethra $D_{10}$-values for single-shot urethra-sparing (boost therapy) for 26 patients. $^{169}$Yb-based RSBT improved mean prostate $D_{90}$ by 6.4 Gy (28%) and reduced urethra $D_{10}$ by 2.4 Gy (22%) relative to conventional HDR-BT for dose escalation and urethra-sparing plans, respectively. FIG. 9B illustrates delivery times for the delivery techniques of FIG. 9A. Definitions: $D_{90}$=minimum dose to the hottest 90% of the prostate; $D_{10}$=minimum dose to the hottest 10% of the urethra; HDR-BT=high-dose-rate brachytherapy delivered with $^{192}$Ir, RSBT=rotating shield brachytherapy delivered with $^{169}$Yb. As shown in FIG. 9A, the use of RSBT for prostate dose escalation in the monotherapy setting resulted in substantial dosimetric gains, with a mean (±1 standard deviation) prostate $D_{90}$ increase from 22.55±0.0 Gy for HDR-BT to 28.6±1.0 Gy for RSBT, a 6.4 Gy (28%) mean prostate $D_{90}$ increase with no increase in urethra $D_{10}$. Dose escalation delivery times for HDR-BT were 15.5±2.2 minutes (10.0 Ci of $^{192}$Ir) to 36.0±5.2 minutes (4.3 Ci of $^{192}$Ir), and delivery times for RSBT were longer at 48.6±5.9 minutes (27.0 Ci of $^{169}$Yb) to 113.0±13.6 minutes (11.6 Ci of $^{169}$Yb). RSBT provided a substantial dosimetric benefit for urethra-sparing, a urethra $D_{10}$ decrease from 15.7±0.3 Gy for HDR-BT to 12.4±0.5 Gy for RSBT, a 3.4 Gy (22%) reduction without compromising prostate $D_{90}$. Urethra-sparing RSBT delivery times for HDR-BT were 11.4±1.7 minutes (10.0 Ci of $^{192}$Ir) to 26.4±3.9 minutes (4.3 Ci of $^{192}$Ir), and delivery times for RSBT were longer at 28.2±3.8 minutes (27.0 Ci of $^{169}$Yb) to 65.4±8.8 minutes (11.6 Ci of $^{169}$Yb). These dosimetric improvements also represent potentially clinically significant gains with feasible delivery times.

As disclosed herein, robotic rotating shield brachytherapy (RSBT) can provide the opportunity to deliver radiation dose distributions that are far more conformal to the prostate than conventional HDR-BT with rectal, bladder, and urethral avoidance. For monotherapy, single-shot RSBT can provide prostate doses escalated beyond those possible with HDR-BT without increasing urethral dose, potentially improving long-term biochemical control. For boost therapy, single-shot RSBT can provide a lower urethra dose than HDR-BT, achieving urethral sparing and potentially reducing toxicity without compromising long-term biochemical control. Robotic RSBT is not restricted to the single-shot (single-fraction) paradigm and could be delivered over multiple fractions, similar to conventional HDR-BT fractionation regimens, if desired. Other benefits of RSBT are possible for prostate cancer patients, including optimizing the tradeoff between dose escalation and urethral sparing for monotherapy, wherein a clinically-relevant prostate dose coverage goal, such as $D_{90}$ is met, and the urethra, rectum, and bladder doses are reduced below those of conventional HDR-BT. In such an example the clinical goal may not be to maximize the prostate dose without violating the bladder, rectum, or urethra dose tolerances for those organs at risk (OARs), but to minimize the doses to the OARs while meeting a prostate dose goal that would be expected to result in a biochemical control probability at some number of years post-treatment, for example 95% biochemical control at 6 years post-treatment.

A radiation source with a lower average energy than conventional $^{192}$Ir can be used to deliver robotic RSBT. Known radioisotope options for such sources are $^{131}$Cs, $^{125}$I, $^{103}$Pd, $^{198}$Au, $^{187}$W, $^{169}$Yb, $^{170}$Tm, $^{145}$Sm, $^{137}$Cs, $^{153}$Gd, $^{109}$Cd, $^{65}$Zn, $^{75}$Se, $^{56}$Co, $^{57}$Co, $^{58}$Co, or $^{60}$Co.

Computing Device

Figure 10:
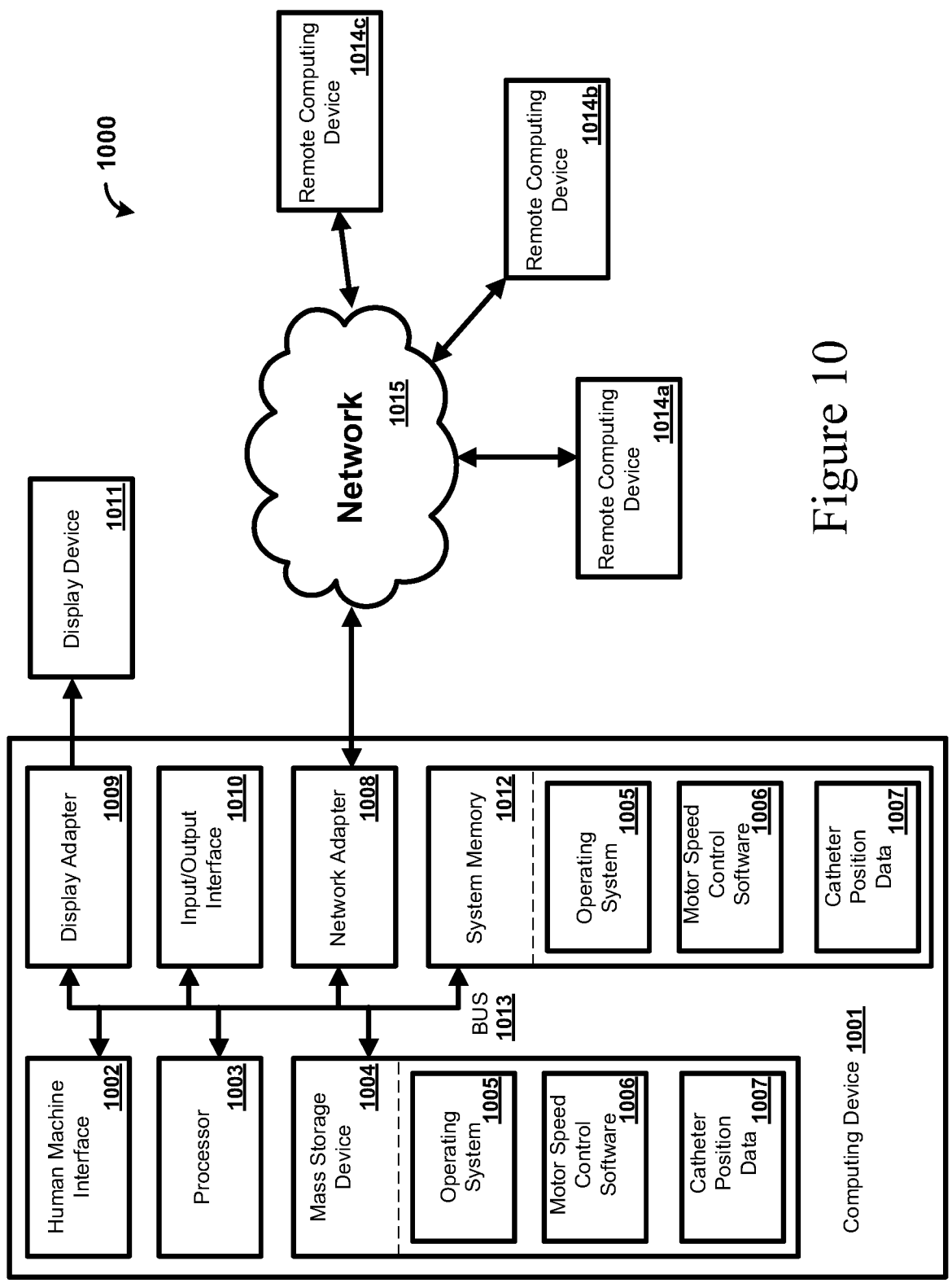
FIG. 10 shows a computing system including an exemplary configuration of a computing device for use with the RSBT system disclosed herein.

FIG. 10 shows a system 1000 including an exemplary configuration of a computing device 1001 for use with the RSBT system 100. In some aspects, the computing device 1001 can be an on-board controller. In further aspects, it is contemplated that a separate computing device, such as, for example, a tablet, laptop, or desktop computer can communicate with the RSBT system 100 and can enable an operator to interface with the RSBT system 100. In still further aspects, it is contemplated that a plurality of computing devices (e.g., an on-board controller and a personal computer) can cooperate to control the movement and monitoring of the movement and position of the robotic positioning system 102, the catheter drive assembly 200, the catheter 302, and the afterloader. In some aspects, the robotic positioning system 102 can comprise an override that enables manual control of at least one of the degrees of freedom of the robotic positioning system over the computing device 1001.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as catheter position data 1007 (i.e., data from signals received by the electrodes) and/or program modules such as operating system 1005 and motor speed control software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EE-PROM), and the like.

Any number of program modules may be stored on the mass storage device 1004. An operating system 1005 and motor speed control software 1006 may be stored on the mass storage device 1004. One or more of the operating system 1005 and motor speed control software 1006 (or some combination thereof) may comprise program modules and the motor speed control software 1006. Catheter position data 1007 may also be stored on the mass storage device 1004. Catheter position data 1007 may be stored in any of one or more databases known in the art. The databases may be centralized or distributed across multiple locations within the network 1015.

A user may enter commands and information into the computing device 1001 using an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like. These and other input devices may be connected to the one or more processors 1003 using a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 using an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 using Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014a,b,c. A remote computing device 1014a,b,c may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014a,b,c may be made using a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet. It is contemplated that the remote computing devices 1014a,b,c can optionally have some or all of the components disclosed as being part of computing device 1001.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A rotating shield brachytherapy (RSBT) apparatus comprising: a radiation source; at least one applicator that is configured to be inserted or implanted into a patient; a catheter having an outer surface and opposed proximal and distal end portions and a longitudinal axis extending along the length of the catheter, wherein the distal end portion of the catheter comprises at least one radiation shield and is configured to receive a wire-mounted radiation source (such as, for example, from an afterloader device); a catheter drive assembly that is configured to cause helical motion of the catheter, wherein the catheter drive assembly is configured to engage the proximal end portion of the catheter to selectively rotate the catheter about the longitudinal axis; a robotic positioning system that is configured to align the catheter drive assembly, in both position and angular orientation at a modifiable rate, with the at least one applicator, or to any programmed point in space; and a connection system that is configured to couple the catheter drive assembly to the at least one applicator, and further configured to decouple the catheter drive from the at least one applicator, wherein, when the at least one applicator is coupled to the catheter drive assembly, the catheter is configured to be advanced into, and out of, the at least one applicator at a variable rate through operation of the catheter drive assembly.

Aspect 2: The RSBT apparatus of aspect 1, wherein the at least one radiation shield comprises radiation-blocking material.

Aspect 3: The RSBT apparatus of aspect 2, wherein the radiation-blocking material has a modifiable thickness.

Aspect 4: The RSBT apparatus of aspect 2 or aspect 3, wherein the at least one radiation shield defines at least one radiation window that allows radiation to exit the catheter.

Aspect 5: The RSBT apparatus of aspect 2 or aspect 3, wherein the at least one radiation shield defines at least one radiation window of varying angular width and longitudinal thickness that allows radiation to exit the catheter.

Aspect 6: The RSBT apparatus of any one of the preceding aspects, wherein the distal end portion of the catheter comprises at least one axial position along the longitudinal axis of the catheter at which no radiation shield is present.

Aspect 7: The RSBT apparatus of any one of the preceding aspects, wherein a proximal side of the catheter drive assembly is configured to receive a transfer tube from a remote afterloader to permit control of the position of the radiation source wire in the catheter.

Aspect 8: The RSBT apparatus of any one of the preceding aspects, wherein a receiver for a connector on the catheter drive assembly is affixed to a proximal end of one or more of the at least one applicator.

Aspect 9: The RSBT apparatus of any one of the preceding aspects, wherein the catheter drive assembly is configured for attachment to a proximal end portion of the at least one applicator.

Aspect 10: The RSBT apparatus of any one of the preceding aspects, further comprising one or more linear actuators, wherein the connector between the at least one applicator and the catheter drive assembly is actuated by the one or more linear actuators.

Aspect 11: The RSBT apparatus of claim 10, wherein the one or more linear actuators comprises a plurality of linear actuators, and wherein at least one linear actuator of the plurality of linear actuators is redundant.

Aspect 12: The RSBT apparatus of any one of the preceding aspects, wherein the connection system facilitates the automated docking of the catheter drive assembly to the receiver on each applicator of the at least one applicator.

Aspect 13: The RSBT apparatus of any one of the preceding aspects, wherein at least one guidance system facilitates the robotic positioning system's alignment and orientation of the catheter drive assembly for connection to the at least one applicator.

Aspect 14: The RSBT apparatus of aspect 13, wherein the at least one guidance system comprises a plurality of guidance systems, and wherein at least one guidance system of the plurality of guidance systems is redundant.

Aspect 15: The RSBT apparatus of aspect 13 or aspect 14, wherein the at least one guidance system is an optical system.

Aspect 16: The RSBT apparatus of aspect 13 or aspect 14, wherein the at least one guidance system is an electrical system.

Aspect 17: The RSBT apparatus of aspect 13 or aspect 14, wherein the at least one guidance system is a magnetic system.

Aspect 18: The RSBT apparatus of aspect 13 or aspect 14, wherein the at least one guidance system can be interchanged between optical, an electrical system, or a magnetic system.

Aspect 19: The RSBT apparatus of aspect 13 or aspect 14, wherein the at least one guidance system is mounted to the catheter drive assembly.

Aspect 20: The RSBT apparatus of any one of the preceding aspects, wherein the catheter drive assembly comprises a catheter receiver with an inner surface that is at least partially helically threaded, and the outer surface of the proximal portion of the catheter is at least partially helically threaded, and the catheter receiver and proximal catheter are configured to complementarily engage each other to permit advancement of the catheter in the distal or proximal direction along the length of the at least one applicator with the linear advancement of the catheter controlled by rotational motion of the catheter relative to the catheter receiver.

Aspect 21: The RSBT apparatus of any one of the preceding aspects, wherein a first applicator of the at least one applicator is at least partially curved.

Aspect 22: The RSBT apparatus of any one of the preceding aspects, wherein the catheter is sufficiently flexible to traverse a curved applicator and sufficiently rigid to transfer rotational motion to the least one radiation shield.

Aspect 23: The apparatus of any one of the preceding aspects, wherein a first applicator of the at least one applicator is straight or substantially straight.

Aspect 24: The RSBT apparatus of any one of the preceding aspects, wherein the robotic positioning system comprises one or more independently controlled motorized carriage rails that are overlaid upon each other to provide translational motion of the catheter drive assembly along one or more dimensions.

Aspect 25: The RSBT apparatus of any one of the preceding aspects, wherein the robotic positioning system comprises one or more independently controlled robotic rotary motors to provide rotational motion of the catheter drive assembly along one or more dimensions.

Aspect 26: The RSBT apparatus of any one of the preceding aspects, wherein the robotic positioning system has a manual override capability for one or more degrees of freedom of motion.

Aspect 27: The RSBT apparatus of any one of the preceding aspects, wherein the catheter defines a lumen that is configured to receive the radiation source, and wherein the lumen is either partially aligned or substantially aligned with the longitudinal axis of the catheter, and wherein the lumen is partially radially offset from the longitudinal axis of the catheter.

Aspect 28: The RSBT apparatus of any one of the preceding aspects, wherein the catheter defines a lumen that is configured to receive the radiation source, and wherein the lumen is aligned or substantially aligned with the longitudinal axis of the catheter.

Aspect 29: The RSBT apparatus of any one of the preceding aspects, wherein the catheter drive assembly comprises a locking mechanism for the catheter that prevents longitudinal motion of the catheter and allows rotational motion of the catheter.

Aspect 30: The RSBT apparatus of any one of the preceding aspects, wherein the catheter drive assembly comprises one or more rotational motors that are mechanically coupled to the catheter.

Aspect 31: The RSBT apparatus of aspect 30, wherein the one or more rotational motors comprises a plurality of rotational motors, and wherein at least one rotational motor of the plurality of rotational motors is redundant.

Aspect 32: The RSBT apparatus of any one of the preceding aspects, wherein the catheter drive assembly can be disconnected en bloc from the robotic positioning system and substituted for a replacement, or similarly configured, catheter drive assembly.

Aspect 33: The RSBT apparatus of any one of the preceding aspects, wherein the catheter drive assembly comprises a catheter position monitoring system that tracks a position of the catheter in real time, wherein the position of the catheter comprises at least one of an angular position or a longitudinal position.

Aspect 34: The RSBT apparatus of aspect 33, wherein the catheter position monitoring system produces readings that are processed by comparing the catheter position to an expected catheter position in a feedback loop in which the catheter position is corrected to decrease a difference between the catheter position and the expected catheter position.

Aspect 35: The RSBT apparatus of any one of the preceding aspects wherein the at least one applicator is an interstitial applicator.

Aspect 36: The RSBT apparatus of any one of the preceding aspects, wherein the at least one applicator is an intracavitary applicator.

Aspect 37: The RSBT apparatus of any one of the preceding aspects, wherein the at least one applicator is an intraluminal applicator.

Aspect 38: The RSBT apparatus of any one of the preceding aspects, wherein the at least one applicator comprises one or more optically transparent or translucent portions.

Aspect 39: The RSBT apparatus of aspect 38, wherein the optically transparent or translucent portions of the at least one applicator comprise internal or external markings that are configured to permit measurement of longitudinal position and/or angular position of the catheter.

Aspect 40: The RSBT apparatus of aspect 38 or aspect 39, wherein the optically transparent or translucent potions comprise internal or external markings that are configured to permit measurement of an axial location of the catheter and/or a radiation source wire within the catheter.

Aspect 41: A method of assembling an RSBT apparatus of any one of the preceding aspects.

Aspect 42: A method of using an RSBT apparatus of any one of aspects 1-40.

Those skilled in the art will recognize, or be able to ascertain using no more than routine experimentation, many equivalents to the specific embodiments of the method and compositions described herein. Such equivalents are intended to be encompassed by the following claims.

The following list of references are hereby incorporated by reference herein for all purposes.

1. R. L. Siegel, K. D. Miller and A. Jemal, "Cancer statistics, 2019," CA Cancer J Clin 69, 7-34 (2019).
2. A. M. Noone, N. Howlader, M. Krapcho, D. Miller, A. Brest, M. Yu, J. Ruhl, Z. Tatalovich, A. Mariotto, D. R. Lewis, H. S. Chen, E. J. Feuer and K. A. Cronin, "SEER Cancer Statistics Review, 1975-2015, National Cancer Institute. Bethesda, Md.," Vol. 2019, (https://seer.cancer.gov/csr/1975_2015/, based on November 2017 SEER data submission, posted to the SEER web site, April 2018, 2018).
3. R. C. Chen, J. A. Clark and J. A. Talcott, "Individualizing quality-of-life outcomes reporting: how localized prostate cancer treatments affect patients with different levels of baseline urinary, bowel, and sexual function," J Clin Oncol 27, 3916-3922 (2009).
4. M. J. Zelefsky, Z. Fuks, M. Hunt, Y. Yamada, C. Marion, C. C. Ling, H. Amols, E. S. Venkatraman and S. A. Leibel, "High-dose intensity modulated radiation therapy for prostate cancer: early toxicity and biochemical outcome in 772 patients," Int J Radiat Oncol 53, 1111-1116 (2002).
5. P. D. Grimm, J. C. Blasko, J. E. Sylvester, R. M. Meier and W. Cavanagh, "10-year biochemical (prostate-specific antigen) control of prostate cancer with (125)I brachytherapy," Int J Radiat Oncol Biol Phys 51, 31-40 (2001).
6. Y. Yoshioka, T. Nose, K. Yoshida, R. J. Oh, Y. Yamada, E. Tanaka, H. Yamazaki and T. Inoue, "High-dose-rate brachytherapy as monotherapy for localized prostate cancer: a retrospective analysis with special focus on tolerance and chronic toxicity," Int J Radiat Oncol Biol Phys 56, 213-220 (2003).
7. J. E. Sylvester, P. D. Grimm, J. C. Blasko, J. Millar, P. F. Orio, 3rd, S. Skoglund, R. W. Galbreath and G. Merrick, "15-Year biochemical relapse free survival in clinical Stage T1-T3 prostate cancer following combined external beam radiotherapy and brachytherapy; Seattle experience," Int J Radiat Oncol Biol Phys 67, 57-64 (2007).
8. P. Grimm, I. Billiet, D. Bostwick, A. P. Dicker, S. Frank, J. Immerzeel, M. Keyes, P. Kupelian, W. R. Lee, S. Machtens, J. Mayadev, B. J. Moran, G. Merrick, J. Millar, M. Roach, R. Stock, K. Shinohara, M. Scholz, E. Weber, A. Zietman, M. Zelefsky, J. Wong, S. Wentworth, R. Vera and S. Langley, "Comparative analysis of prostate-specific antigen free survival outcomes for patients with low, intermediate and high risk prostate cancer treatment by radical therapy. Results from the Prostate Cancer Results Study Group," BJU international 109 Suppl 1, 22-29 (2012).
9. R. L. Siegel, K. D. Miller and A. Jemal, "Cancer Statistics, 2017," CA Cancer J Clin 67, 7-30 (2017).
10. M. G. Sanda, R. L. Dunn, J. Michalski, H. M. Sandler, L. Northouse, L. Hembroff, X. Lin, T. K. Greenfield, M. S. Litwin, C. S. Saigal, A. Mahadevan, E. Klein, A. Kibel, L. L. Pisters, D. Kuban, I. Kaplan, D. Wood, J. Ciezki, N. Shah and J. T. Wei, "Quality of life and satisfaction with outcome among prostate-cancer survivors," N Engl J Med 358, 1250-1261 (2008).
11. E. Haglind, S. Carlsson, J. Stranne, A. Wallerstedt, U. Wilderang, T. Thorsteinsdottir, M. Lagerkvist, J. E. Damber, A. Bjartell, J. Hugosson, P. Wiklund, G. Steineck and L. s. committee, "Urinary Incontinence and Erectile Dysfunction After Robotic Versus Open Radical Prostatectomy: A Prospective, Controlled, Nonrandomised Trial," Eur Urol 68, 216-225 (2015).
12. M. Avila, V. Becerra, F. Guedea, J. F. Suarez, P. Fernandez, V. Macias, A. Marino, A. Hervas, I. Herruzo, M. J. Ortiz, J. Ponce de Leon, G. Sancho, O. Cunillera, Y. Pardo, F. Cots, M. Ferrer and C. Multicentric Spanish Group of Clinically Localized Prostate, "Estimating preferences for treatments in patients with localized prostate cancer," Int J Radiat Oncol Biol Phys 91, 277-287 (2015).
13. M. R. Cooperberg, N. R. Ramakrishna, S. B. Duff, K. E. Hughes, S. Sadownik, J. A. Smith and A. K. Tewari, "Primary treatments for clinically localised prostate cancer: a comprehensive lifetime cost-utility analysis," BJU international 111, 437-450 (2013).
14. N. Mohammed, L. Kestin, M. Ghilezan, D. Krauss, F. Vicini, D. Brabbins, G. Gustafson, H. Ye and A. Martinez, "Comparison of acute and late toxicities for three modern high-dose radiation treatment techniques for localized prostate cancer," Int J Radiat Oncol 82, 204-212 (2012).
15. D. C. Chade, S. F. Shariat, A. M. Cronin, C. J. Savage, R. J. Karnes, M. L. Blute, A. Briganti, F. Montorsi, H. G. van der Poel, H. Van Poppel, S. Joniau, G. Godoy, A. Hurtado-Coll, M. E. Gleave, M. Dall'Oglio, M. Srougi, P. T. Scardino and J. A. Eastham, "Salvage radical prostatectomy for radiation-recurrent prostate cancer: a multi-institutional collaboration," Eur Urol 60, 205-210 (2011).
16. G. Morton, H. T. Chung, M. McGuffin, J. Helou, L. D'Alimonte, A. Ravi, P. Cheung, E. Szumacher, S. Liu, M. Al-Hanaqta, L. Zhang, A. Mamedov and A. Loblaw, "Prostate high dose-rate brachytherapy as monotherapy for low and intermediate risk prostate cancer: Early toxicity and quality-of life results from a randomized phase II clinical trial of one fraction of 19 Gy or two fractions of 13.5 Gy," Radiother Oncol 122, 87-92 (2017).
17. P. Hoskin, A. Rojas, P. Ostler, R. Hughes, R. Alonzi, G. Lowe and L. Bryant, "High-dose-rate brachytherapy alone given as two or one fraction to patients for locally advanced prostate cancer: acute toxicity," Radiother Oncol 110, 268-271 (2014).
18. D. J. Krauss, H. Ye, A. A. Martinez, B. Mitchell, E. Sebastian, A. Limbacher and G. S. Gustafson, "Favor- 18. able Preliminary Outcomes for Men With Low- and Intermediate-risk Prostate Cancer Treated With 19-Gy Single-fraction High-dose-rate Brachytherapy," Int J Radiat Oncol Biol Phys 97, 98-106 (2017).
19. P. J. Prada, M. Ferri, J. Cardenal, A. G. Blanco, J. Anchuelo, I. Diaz de Cerio, A. Vazquez, M. Pacheco, I. Raba and S. Ruiz, "High-dose-rate interstitial brachytherapy as monotherapy in one fraction of 20.5 Gy for the treatment of localized prostate cancer: Toxicity and 6-year biochemical results," Brachytherapy 17, 845-851 (2018).
20. Z. A. Siddiqui, G. S. Gustafson, H. Ye, A. A. Martinez, B. Mitchell, E. Sebastian, A. Limbacher and D. J. Krauss, "5-Year Outcomes of a Single Institution Prospective Trial of 19 Gy Single-Fraction HDR Brachytherapy for Low- and Intermediate-Risk Prostate Cancer," Int J Radiat Oncol Biol Phys In Press (2019).
21. H. Hauswald, M. R. Kamrava, J. M. Fallon, P. C. Wang, S. J. Park, T. Van, L. Borja, M. L. Steinberg and D. J. Demanes, "High-Dose-Rate Monotherapy for Localized Prostate Cancer: 10-Year Results," Int J Radiat Oncol Biol Phys 94, 667-674 (2016).
22. M. S. Jawad, J. T. Dilworth, G. S. Gustafson, H. Ye, M. Wallace, A. Martinez, P. Y. Chen and D. J. Krauss, "Outcomes Associated With 3 Treatment Schedules of High-Dose-Rate Brachytherapy Monotherapy for Favorable-Risk Prostate Cancer," Int J Radiat Oncol Biol Phys 94, 657-666 (2016).
23. I. C. Hsu, K. Bae, K. Shinohara, J. Pouliot, J. Purdy, G. Ibbott, J. Speight, E. Vigneault, R. Ivker and H. Sandler, "Phase II trial of combined high-dose-rate brachytherapy and external beam radiotherapy for adenocarcinoma of the prostate: preliminary results of RTOG 0321," Int J Radiat Oncol Biol Phys 78, 751-758 (2010).
24. T. Akimoto, H. Katoh, S. E. Noda, K. Ito, T. Yamamoto, B. Kashiwagi and T. Nakano, "Acute genitourinary toxicity after high dose rate (HDR) brachytherapy combined with hypofractionated external-beam radiation therapy for localized prostate cancer: Second analysis to determine the correlation between the urethral dose in HDR brachytherapy and the severity of acute genitourinary toxicity," Int J Radiat Oncol Biol Phys 63, 472-478 (2005).
25. G. C. Morton, D. A. Loblaw, H. Chung, G. Tsang, R. Sankreacha, A. Deabreu, L. Zhang, A. Mamedov, P. Cheung, D. Batchelar, C. Danjoux and E. Szumacher, "Health-related quality of life after single-fraction high-dose-rate brachytherapy and hypofractionated external beam radiotherapy for prostate cancer," Int J Radiat Oncol Biol Phys 80, 1299-1305 (2011).
26. L. K. Ballas, E. B. Elkin, D. Schrag, B. D. Minsky and P. B. Bach, "Radiation therapy facilities in the United States," Int J Radiat Oncol Biol Phys 66, 1204-1211 (2006).
27. IMV, "Radiation Therapy Market Summary Report," (2016).
28. U.S. Patent WO 2018/112625 A1
29. G. Famulari and S. A. Enger, "A Novel Delivery System for High Dose Rate Intensity Modulated Brachytherapy with Intermediate Energy Brachytherapy Radiation Sources such as $^{169}$Yb," Brachytherapy 16, S23 (2017).
30. H. Dadkhah, K. M. Hopfensperger, Y. Kim, X. Wu and R. T. Flynn, "Multisource Rotating Shield Brachytherapy Apparatus for Prostate Cancer," Int J Radiat Oncol Biol Phys (2017).
31. Q. Adams, K. M. Hopfensperger, Y. Kim, X. Wu, W. Xu, H. Shukla, J. McGee, J. M. Caster and R. T. Flynn, "Effectiveness of Rotating Shield Brachytherapy for Prostate Cancer Dose Escalation and Urethral Sparing," Int J Radiat Oncol Biol Phys (2018).
32. M. Cho, X. Wu, H. Dadkhah, J. Yi, R. T. Flynn, Y. Kim and W. Xu, "Fast dose optimization for rotating shield brachytherapy," Med Phys 44, 5384-5392 (2017).
33. G. C. Morton, D. A. Loblaw, R. Sankreacha, A. Deabreu, L. Zhang, A. Mamedov, P. Cheung, B. Keller, C. Danjoux, E. Szumacher and G. Thomas, "Single-fraction high-dose-rate brachytherapy and hypofractionated external beam radiotherapy for men with intermediate-risk prostate cancer: analysis of short- and medium-term toxicity and quality of life," International journal of radiation oncology, biology, physics 77, 811-817 (2010).
34. R. Pötter, K. Tanderup, C. Kirisits, A. de Leeuw, K. Kirchheiner, R. Nout, L. T. Tan, C. Haie-Meder, U. Mahantshetty, B. Segedin, P. Hoskin, K. Bruheim, B. Rai, F. Huang, E. Van Limbergen, M. Schmid, N. Nesvacil, A. Sturdza, L. Fokdal, N. B. K. Jensen, D. Georg, M. Assenholt, Y. Seppenwoolde, C. Nomden, I. Fortin, S. Chopra, U. van der Heide, T. Rumpold, J. C. Lindegaard, I. Jurgenliemk-Schulz and E. C. Group, "The EMBRACE II study: The outcome and prospect of two decades of evolution within the GEC-ESTRO GYN working group and the EMBRACE studies," Clin Transl Radiat Oncol 9, 48-60 (2018).
35. D. L. Mason, J. J. Battista, R. B. Barnett and A. T. Porter, "Ytterbium-169: calculated physical properties of a new radiation source for brachytherapy," Med Phys 19, 695-703 (1992).
36. M. A. Ebert, "Possibilities for intensity-modulated brachytherapy: technical limitations on the use of non-isotropic sources," Phys Med Biol 47, 2495-2509 (2002).
37. D. C. Medich, M. A. Tries and J. J. Munro, 2nd, "Monte Carlo characterization of an ytterbium-169 high dose rate brachytherapy source with analysis of statistical uncertainty," Med Phys 33, 163-172 (2006).
38. L. Lin, R. R. Patel, B. R. Thomadsen and D. L. Henderson, "The use of directional interstitial sources to improve dosimetry in breast brachytherapy," Med Phys 35, 240-247 (2008).
39. H. Park, D. -H. Kwon, Y. H. Cha, T. -S. Kim, J. Han, K. -H. Ko, D. -Y. Jeong and C. -J. Kim, "Stable isotope production of 168Yb and 176Yb for industrial and medical applications," Journal of Nuclear Science and Technology S6, 111-116 (2008).
40. J. J. VanDamme, W. S. Culberson, L. A. DeWerd and J. A. Micka, "Air-kerma strength determination of a 169Yb high dose rate brachytherapy source," Med Phys 35, 3935-3942 (2008).
41. M. J. Price, K. A. Gifford, J. L. Horton, Jr., P. J. Eifel, M. T. Gillin, A. A. Lawyer and F. Mourtada, "Monte Carlo model for a prototype CT-compatible, anatomically adaptive, shielded intracavitary brachytherapy applicator for the treatment of cervical cancer," Med Phys 36, 4147-4155 (2009).
42. C. Shi, B. Guo, C. Y. Cheng, C. Esquivel, T. Eng and N. Papanikolaou, "Three dimensional intensity modulated brachytherapy (IMBT): dosimetry algorithm and inverse treatment planning," Med Phys 37, 3725-3737 (2010).

43. S. A. Enger, H. Lundkvist, M. D'Amours and L. Beaulieu, "Exploring $^{57}$Co as a new isotope for brachytherapy applications," Med Phys 39, 2342-2345 (2012).
44. S. A. Enger, M. D'Amours and L. Beaulieu, "Modeling a hypothetical 170Tm source for brachytherapy applications," Med Phys 38, 5307-5310 (2011).
45. W. Yang, Y. Kim, X. Wu, Q. Song, Y. Liu, S. K. Bhatia, W. Sun and R. T. Flynn, "Rotating-shield brachytherapy for cervical cancer," Phys Med Biol 58, 3931-3941 (2013).
46. Y. Liu, R. T. Flynn, W. Yang, Y. Kim, S. K. Bhatia, W. Sun and X. Wu, "Rapid emission angle selection for rotating-shield brachytherapy," Med Phys 40, 051720 (2013).
47. Y. Liu, R. T. Flynn, Y. Kim, W. Yang and X. Wu, "Dynamic rotating-shield brachytherapy," Med Phys 40, 121703 (2013).
48. M. J. Webster, S. Devic, T. Vuong, D. Yup Han, J. C. Park, D. Scanderbeg, J. Lawson, B. Song, W. Tyler Watkins, T. Pawlicki and W. Y. Song, "Dynamic modulated brachytherapy (DMBT) for rectal cancer," Med Phys 40, 011718 (2013).
49. M. J. Webster, S. Devic, T. Vuong, D. Y. Han, D. Scanderbeg, D. Choi, B. Song and W. Y. Song, "HDR brachytherapy of rectal cancer using a novel grooved-shielding applicator design," Med Phys 40, 091704 (2013).
50. D. Y. Han, M. J. Webster, D. J. Scanderbeg, C. Yashar, D. Choi, B. Song, S. Devic, A. Ravi and W. Y. Song, "Direction-modulated brachytherapy for high-dose-rate treatment of cervical cancer. I: theoretical design," Int J Radiat Oncol Biol Phys 89, 666-673 (2014).
51. Q. E. Adams, J. Xu, E. K. Breitbach, X. Li, S. A. Enger, W. R. Rockey, Y. Kim, X. Wu and R. T. Flynn, "Interstitial rotating shield brachytherapy for prostate cancer," Med Phys 41, 051703 (2014).
52. Y. Liu, R. T. Flynn, Y. Kim and X. Wu, "Asymmetric dose-volume optimization with smoothness control for rotating-shield brachytherapy," Med Phys 41, 111709 (2014).
53. H. Dadkhah, Y. Kim, X. Wu and R. T. Flynn, "Multihelix rotating shield brachytherapy for cervical cancer," Med Phys 42, 6579-6588 (2015).
54. Y. Liu, R. T. Flynn, Y. Kim, H. Dadkhah, S. K. Bhatia, J. M. Buatti, W. Xu and X. Wu, "Paddle-based rotating-shield brachytherapy," Med Phys 42, 5992-6003 (2015).
55. D. Y. Han, H. Safigholi, A. Soliman, A. Ravi, E. Leung, D. J. Scanderbeg, Z. Liu, A. Owrangi and W. Y. Song, "Direction Modulated Brachytherapy for Treatment of Cervical Cancer. II: Comparative Planning Study With Intracavitary and Intracavitary-Interstitial Techniques," Int J Radiat Oncol Biol Phys 96, 440-448 (2016).
56. A. S. Soliman, A. Elzibak, H. Easton, J. Y. Kim, D. Y. Han, H. Safigholi, S. Mashouf, A. Owrangi, A. Ravi and W. Y. Song, "Quantitative MRI assessment of a novel direction modulated brachytherapy tandem applicator for cervical cancer at 1.5 T," Radiother Oncol 120, 500-506 (2016).
57. A. S. Soliman, A. Owrangi, A. Ravi and W. Y. Song, "Metal artefacts in MRI-guided brachytherapy of cervical cancer," J Contemp Brachytherapy 8, 363-369 (2016).
58. A. H. Elzibak, P. M. Kager, A. Soliman, M. R. Paudel, H. Safigholi, D. Y. Han, A. Karotki, A. Ravi and W. Y. Song, "Quantitative CT assessment of a novel direction-modulated brachytherapy tandem applicator," Brachytherapy 17, 465-475 (2018).
59. H. Safigholi, D. Y. Han, S. Mashouf, A. Soliman, A. S. Meigooni, A. Owrangi and W. Y. Song, "Direction modulated brachytherapy (DMBT) for treatment of cervical cancer: A planning study with (192) Ir, (60) Co, and (169) Yb HDR sources," Med Phys 44, 6538-6547 (2017).
60. H. Safigholi, A. S. Meigooni and W. Y. Song, "Comparison of (192) Ir, (169) Yb, and (60) Co high-dose rate brachytherapy sources for skin cancer treatment," Med Phys 44, 4426-4436 (2017).
61. G. Famulari, T. Urlich, A. Armstrong and S. A. Enger, "Practical aspects of (153)Gd as a radioactive source for use in brachytherapy," Appl Radiat Isot 130, 131-139 (2017).

What is claimed is:

1. A rotating shield brachytherapy (RSBT) apparatus comprising:
   a radiation source coupled to a radiation source wire;
   at least one applicator that is configured to be inserted or implanted into a patient;
   a catheter having an outer surface and opposed proximal and distal end portions and a longitudinal axis extending along a length of the catheter, wherein the distal end portion of the catheter comprises at least one radiation shield and is configured to receive the radiation source coupled to the radiation source wire;
   a catheter drive assembly that is configured to cause helical motion of the catheter, wherein the catheter drive assembly is configured to engage the proximal end portion of the catheter to selectively rotate the catheter about the longitudinal axis;
   a robotic positioning system that is configured to align the catheter drive assembly, in both position and angular orientation at a modifiable rate, with the at least one applicator, or to any programmed point in space; and
   a connection system that is configured to couple the catheter drive assembly to the at least one applicator, and further configured to decouple the catheter drive from the at least one applicator,
   wherein, when the at least one applicator is coupled to the catheter drive assembly, the catheter is configured to be advanced into, and out of, the at least one applicator at a variable rate through operation of the catheter drive assembly.

2. The RSBT apparatus of claim 1, wherein the at least one radiation shield comprises radiation-blocking material.

3. The RSBT apparatus of claim 2, wherein the at least one radiation shield defines at least one radiation window that allows radiation to exit the catheter.

4. The RSBT apparatus of claim 1, wherein the at least one applicator comprises one or more optically transparent or translucent portions.

5. The RSBT apparatus of claim 1, wherein the catheter drive assembly comprises a catheter position monitoring system that tracks a position of the catheter in real time, wherein the position of the catheter comprises at least one of an angular position or a longitudinal position.

6. The RSBT apparatus of claim 1, wherein the distal end portion of the catheter comprises at least one axial position along the longitudinal axis of the catheter at which no radiation shield is present.

7. The RSBT apparatus of claim 1, wherein a proximal side of the catheter drive assembly is configured to receive a transfer tube from a remote afterloader to permit control of a position of the radiation source wire in the catheter.

8. The RSBT apparatus of claim 1, wherein a receiver for a connector on the catheter drive assembly is affixed to a proximal end of one or more of the at least one applicator.

9. The RSBT apparatus of claim 1, wherein the catheter drive assembly is configured for attachment to a proximal end portion of the at least one applicator.

10. The RSBT apparatus of claim 1, further comprising one or more linear actuators, wherein the connector between the at least one applicator and the catheter drive assembly is actuated by the one or more linear actuators.

11. The RSBT apparatus of claim 1, wherein the catheter drive assembly comprises one or more rotational motors that are mechanically coupled to the catheter.

12. The RSBT apparatus of claim 1, wherein the catheter drive assembly comprises a locking mechanism for the catheter that prevents longitudinal motion of the catheter and allows rotational motion of the catheter.

13. The RSBT apparatus of claim 1, wherein at least one guidance system facilitates the robotic positioning system's alignment and orientation of the catheter drive assembly for connection to the at least one applicator.

14. The RSBT apparatus of claim 1, wherein the catheter defines a lumen that is configured to receive the radiation source, and wherein the lumen is aligned or substantially aligned with the longitudinal axis of the catheter.

15. The RSBT apparatus of claim 1, wherein the catheter defines a lumen that is configured to receive the radiation source, and wherein the lumen is either partially aligned or substantially aligned with the longitudinal axis of the catheter, and wherein the lumen is partially radially offset from the longitudinal axis of the catheter.

16. The RSBT apparatus of claim 1, wherein the robotic positioning system comprises one or more independently controlled robotic rotary motors to provide rotational motion of the catheter drive assembly along one or more dimensions.

17. The RSBT apparatus of claim 1, wherein the robotic positioning system comprises one or more independently controlled motorized carriage rails that are overlaid upon each other to provide translational motion of the catheter drive assembly along one or more dimensions.

18. The apparatus of claim 1, wherein a first applicator of the at least one applicator is straight or substantially straight.

19. The RSBT apparatus of claim 1, wherein a first applicator of the at least one applicator is at least partially curved.

20. The RSBT apparatus of claim 1, wherein the catheter drive assembly comprises a catheter receiver with an inner surface that is at least partially helically threaded, and the outer surface of the proximal end portion of the catheter is at least partially helically threaded, and the catheter receiver and proximal catheter are configured to complementarily engage each other to permit advancement of the catheter in a distal or proximal direction along a length of the at least one applicator with a linear advancement of the catheter controlled by rotational motion of the catheter relative to the catheter receiver.

* * * * *